(12) United States Patent
Thomas et al.

(10) Patent No.: US 7,280,861 B2
(45) Date of Patent: Oct. 9, 2007

(54) DIAGNOSIS AND CLASSIFICATION OF DISEASE AND DISABILITY USING LOW FREQUENCY MAGNETIC FIELD DESIGNED PULSES (CNPS)

(75) Inventors: Alex Thomas, London (CA); Frank Prato, London (CA); Kevin White, London (CA)

(73) Assignee: Fralex Therapeutics, Inc., Toronto (CA)

(*) Notice: Subject to any disclaimer, the term of this patent is extended or adjusted under 35 U.S.C. 154(b) by 0 days.

(21) Appl. No.: 10/319,944

(22) Filed: Dec. 16, 2002

(65) Prior Publication Data

US 2003/0181791 A1 Sep. 25, 2003

Related U.S. Application Data

(63) Continuation of application No. PCT/CA01/00828, filed on Jun. 7, 2001.

(60) Provisional application No. 60/209,994, filed on Jun. 8, 2000.

(51) Int. Cl.
*A61B 5/05* (2006.01)

(52) U.S. Cl. .................. 600/407; 600/14; 600/300; 600/409; 600/509; 600/544; 600/587

(58) Field of Classification Search .................. 600/9, 600/13, 407, 409, 544, 14, 300, 509, 587; 128/920; 324/244, 248
See application file for complete search history.

(56) References Cited

U.S. PATENT DOCUMENTS 3,678,337 A 7/1972 Grauvogel et al.
4,583,545 A 4/1986 Towe ................ 128/630
4,825,877 A 5/1989 Kempe
5,066,272 A 11/1991 Eaton et al.
5,084,003 A 1/1992 Susic
5,342,410 A 8/1994 Braverman
5,527,259 A 6/1996 Grace et al.
5,621,188 A 4/1997 Lee et al.
5,634,939 A 6/1997 Kuster et al.
5,690,109 A 11/1997 Govind et al.
5,725,471 A 3/1998 Davey
5,807,272 A 9/1998 Kun et al. .............. 600/547
5,833,600 A * 11/1998 Young .................... 600/300
5,935,054 A 8/1999 Loos
6,128,522 A 10/2000 Acker
6,198,958 B1 * 3/2001 Ives et al. ................ 600/411
6,234,953 B1 * 5/2001 Thomas et al. .......... 600/14
6,312,376 B1 11/2001 Koren et al.

(Continued)

FOREIGN PATENT DOCUMENTS

CA 1237783 6/1988

(Continued)

OTHER PUBLICATIONS

Baker, Timothy B., "Morphine Tolerance as Habituation", *Psychological Review*, vol. 92, No. 1, (1985), 78-108.

(Continued)

*Primary Examiner*—Ruth S. Smith
(74) *Attorney, Agent, or Firm*—John S. Child, Jr.

(57) ABSTRACT

The invention is directed to the use of magnetic field designed pulses for the diagnoses and classification of severity of disease states and disability in humans and animals.

21 Claims, 20 Drawing Sheets

U.S. PATENT DOCUMENTS

| | | | |
|---|---|---|---|
| 6,427,089 B1 * | 7/2002 | Knowlton | 607/101 |
| 6,520,903 B1 * | 2/2003 | Yamashiro | 600/9 |
| 6,547,713 B1 | 4/2003 | Talpo | |
| 6,687,525 B2 * | 2/2004 | Llinas et al. | 600/407 |
| 6,719,778 B1 * | 4/2004 | Van Tassel et al. | 607/88 |
| 2002/0169355 A1 | 11/2002 | Rohan | |
| 2003/0023159 A1 | 1/2003 | Philipp | |
| 2003/0181791 A1 | 9/2003 | Thomas | |
| 2003/0217754 A1 | 11/2003 | Thomas | |
| 2006/0106274 A1 | 5/2006 | Thomas | |

FOREIGN PATENT DOCUMENTS

| | | |
|---|---|---|
| CA | 2066204 A1 | 2/1991 |
| DE | 3331976 A1 | 3/1985 |
| DE | 39 38 920 | 5/1991 |
| EP | 1138348 A2 | 10/2001 |
| FR | 2 533 131 | 3/1984 |
| GB | 2025237 | 1/1980 |
| GB | 2143131 | 2/1985 |
| GB | 2270000 | 2/1994 |
| WO | WO-9611723 A1 | 4/1996 |
| WO | WO-97/46277 | 12/1997 |
| WO | WO-9806342 A1 | 2/1998 |
| WO | WO-9847565 A1 | 10/1998 |
| WO | WO-9852465 A1 | 11/1998 |
| WO | WO-0076582 A1 | 12/2000 |
| WO | WO-0232504 A2 | 4/2002 |

OTHER PUBLICATIONS

Baker-Price, L. A., "Weak, But Complex Pulsed Magnetic Fields May Reduce Depression Following Traumatic Brain Injury", *Perceptual and Motor Skills*, 83, (1996), 491-498.

Betancur, Catalina, "Magnetic field effects on stress-induced analgesia in mice: modulation by light", *Neuroscience Letters 182*, (1994), 147-150.

Choleris, E., "Shielding but not zeroing of the ambient magnetic field reduces stress-induced analgesia in mice", *The Royal Society*, (2001).

Del Seppia, Cristina, "Exposure to a Hypogeomagnetic field Or To Oscillating Magnetic Fields Similarly Reduce Stress-Induced Analgesia in C57 Male Mice", *Life Sciences*, vol. 66, No. 14, (2000), 1299-1306.

Deutschlander, Mark E., "The Case for Light-Dependent Magnetic Orientation In Animals", *The Journal of Experimental Biology 202*, (1999), 891-908.

Dyakonova, V. E., "Complex Avoidance Behaviour and its Neurochemical Regulation in the Land Snail *Cepaea nemoralis*", *Gen. Pharmac.*, vol. 26, No. 4, (1995), 773-777.

Grisel, Judith E., et al., "Associative and non-associative mechanisms of morphine analgesic tolerance are neurochemically distinct in the rat spinal cord", *Psychopharmacology 128*, (1996), 248-225.

Kavaliers, Martin, "A Functional Role for an Opiate System in Snail Thermal Behavior", *Science*, vol. 220, (1983), 99-101.

Kavaliers, Martin, "Brief exposure to 60Hz magnetic fields improves sexually dimorphic spatial learning performance in the meadow vole, *Microtus pennsylvanicus*", *Journal of Comparative Physiology A*, 173, (1993), 241-248.

Kavaliers, Martin, "Opioid Systems and Magnetic Field Effects in the Land Snail, *Cepaea nemoralis*", *Biol. Bull. 180*, (Apr. 1991), 301-309.

Kavaliers, Martin, "Opioid Systems and the Biological Effects of Magnetic Fields", *On the Nature of Electromagnetic Field Interactions with Biological Systems, Chapter 13*, (1994), 181-193.

Kavaliers, Martin, "Repeated naloxone treatments and exposures to weak 60-Hz magnetic fields have 'analgesic' effects in snails", *Brain Research*, 620, (1993), 159-162.

Kavaliers, Martin, "Spatial learning in deer mice: sex differences and the effects of endogenous opioids and 60 Hz magnetic fields", *J Comp Physiol A*, 179, (1996), 715-724.

Kavaliers, Martin, et al., "Tolerance to Morphine-Induced Analgesia in Mice: Magnetic Fields Function As Environmental Specific Cues and Reduce Tolerance Development", *Life Sciences*, vol. 37, (1985), 1125-1135.

Kavaliers, M., "Tolerance to the Morphine-Influenced Thermal Response in the Terrestrial Snail, *Cepea Nemoralis*", *Neuropharmacology*, vol. 22, No. 11, (1983), 1321-1326.

Kits, Karel S., "Voltage gated calcium channels in molluscs: classification, Ca2+ dependent inactivation, modulation and functional roles", *Invertebrate Neuroscience*, 2, (1996), 9-34.

Lednev, V. V., "Magnetic Parametric Resonance in Biosystems: Experimental Verification of the Predictions of a theory using regenerating planarians *Dugesia tigrina* as a Test System", *Biophysics*, vol. 41, No. 4, (1996), 825-835.

Mcleod, Kenneth J., "Frequency Dependence of Electric Field Modulation of Fibroblast Protein Synthesis", *Science, New Series*, vol. 236, No. 4807, (1987), 1465-1469.

Michon, Andre, "Attempts to Simulate the Association Between Geomagnetic Activity and Spontaneous Seizures in Rats Using Experimentally Generated Magnetic Fields", *Perceptual and Motor Skills*, 82, (1996), 619-626.

Papi, Floriano, "Exposure to Oscillating Magnetic Fields Influences Sensitivity to Electrical Stimuli. II. Experiments on Humans", *Bioeletromagnetics 16*, (1995), 295-300.

Papi, Floriano, "Orientation-Disturbing Magnetic Treatment Affects The Pigeon Opioid System", *J. exp. Biol.*, 166, (1992), 169-179.

Polk, Charles, "Dosimetry of Extremely-Low-Frequency Magnetic Fields", *Bioeletromagnetics Supplement 1*, (1992), 209-235.

Prato, Frank S., "Attenuation of Morphine-Induced Analgesia in Mice By Exposure to Magnetic Resonance Imaging: Separate Effects Of The Static, Radiofrequency and Time-Varying Magnetic Fields", *Magnetic Resonance Imaging*, vol. 5, (1987), 9-14.

Prato, Frank S., "Behavioural Evidence That Magnetic Filed Effects in the Land Snail, *Cepaea nemoralis*, Might Not Depend on Magnetite or Induced Electric Currents", *Bioelectromagnetics 17*, (1996), 123-130.

Prato, Frank S., "Possible mechanisms by which extremely low frequency magnetic fields affect opioid function", *The FASEB Journal*, vol. 9, (Jun. 1995), 807-814.

Rothman, Richard B., "A Review of the Role of Anti-Opioid Peptides in Morphine Tolerance and Dependence", *Synapse 12*, (1992), 129-138.

Smith, Jr., Laurens H., "Quantified Aspects of Pallial Fluid and Its Affect on the Duration of Locomotor Activity in the Terrestrial Gastropod Triodopsis Albolabris", 407-414.

Thomas, Alex W., "Analgesic Effects of a Specific Pulsed Magnetic Field in the Land Snail, *Cepaea nemoralis*: Consequences of Repeated Exposures, Relations to Tolerance and Cross-Tolerance with DPDPE", *Peptides*, vol. 19, No. 2, (1998), 333-342.

Thomas, Alex W., "Antinociceptive effects of a pulsed magnetic field in the land snail, *Cepaea nemoralis*", *Neuroscience Letters 222*, (1997), 107-110.

Thomas, Alex W., "Daily Post-training Exposure to Pulsed Magnetic Fields That Evoke Morphine-Like Analgesia Affects Consequent Motivation but not Proficiency in Maze Learning in Rats", *Electro- And Magnetobiology*, 16(1), (1997), 33-41.

Thomas, Alex W., "Pulsed Magnetic Field Induced "Analgesia" in the Land Snail, *Cepaea nemoralis*, and the Effects of μ, δ, and κ Opioid Receptor Agonists/Antagonists", *Peptides*, vol. 18, No. 5, (1997), 703-709.

Thomas, A. W., "Rheumatoid Arthritis and Fibromyalgia Patients Exposed to a Specific Pulsed 200 μT Magnetic Field: Effects on Normal Standing Balance.", 74-75.

Tian, Jin-Hua, "Involvement of endogenous Orphanin FQ in electroacupuncture-induced analgesia", *NeuroReport 8*, (1997), 497-500.

Tiffany, Stephen T., "Morphine Tolerance in Rats: Congruence With a Pavlovian Paradigm", *Journal of Comparative and Physiological Psychology*, vol. 95, No. 5, (1981), 747-762.

Tiffany, Stephen, "Tolerance to Morphine in the Rat: Associative and Nonassociative Effects", *Behavioral Neuroscience*, vol. 102, No. 4, (1988), 534-543.

Weaver, James C., "The Response of Living Cells to Very Weak Electric Fields: The Thermal Noise Limit", *Reports*, (1990), 459-462.

Barker, A. T., et al., "Magnetic Stimulation of the Human Brain and Peripheral Nervous Systems: An Introduction and the Results of an Initial Clinical Evaluation", *Neurosurgery*, 20(1), (1987),100-109.

Choleris, E., et al., "A Detailed Ethological Analysis of the Mouse Open Field Test: Effects of Diazepam, Chlordiazepoxide and an Extremely Low Frequency Pulsed Magnetic Field", *Neuroscience and Biobehavioral Reviews*, 25, (2001),235-260.

Prato, F. S., et al., "Extremely Low Frequency Magnetic Fields Can Either Increase or Decrease Analgaesia in the Land Snail Depending on Field and Light Conditions", *Bioelectromagnetics*, 21, (2000),287-301.

Prato, F. S., et al., "Human Standing Balance is Affected by Exposure to Pulsed ELF Magnetic Fields: Light Intensity-Dependent Effects", *NeuroReport*, 12(7), (2001), 1-5.

Thomas, A. W., et al., "A Comparision of Rheumatoid Arthritis and Fibromyalgia Patients and Healty Controls Exposed to a Pulsed (200 μT) Magnetic Field: Effects on Normal Standing Balance", *Neuroscience Letters*, 309, (2001), 17-20.

Thomas, A. W., et al., "Human Subjects Exposed to a Specific Pulsed (200 μT) Magnetic Field: Effects on Normal Standing Balance", *Neuroscience Letters*, 297, (2001),121-124.

Thomas, A. W., et al., "Magnetic Field Exposure and Behavioral Monitoring System", *Bioelectromagnetics*, 22, (2001), 401-407.

Kirschvink, "Particle-size . . . ," Contribution No. 4135 from the division of Geological and Planetary Sciences, California Institute of Technology, pp. 243-256, (1985).

Papi, et al., "Exposure to oscillating magnetic fields . . . ," Bioelectromagnetics, 16:295-300, (1995).

Del Seppia, et al., "Exposure to oscillating magnetic fields influences sensitivity to electrical stimuli I. Experiments on pigeons," Bioelectromagnetics, 16:290-294, (1995).

Bassett, et al., "Treatment of ununited tibial diaphyseal fractures with pulsing electromagnetic fields," J. Bone Joint Surg. 63-A4:511-523, (1981).

Beckers, G and Homberg, V (1991): Impairment of visual perception and visual short term memory scanning by transcranial magnetic stimulation of occipital cortex. Exp Brain Res 87:421-432.

Bell, GB, Marino, AA and Chesson, Al (1992): Alterations in brain electrical activity caused by magnetic fields: Detecting the detection process. Electroenceph Clin Neurophysiol 83:389-397.

Bell, GB, Marino, AA and Chesson, Al (1994): Frequency-specific blocking in the human brain caused by electromagnetic fields. NeuroReport 5:510-512.

Bell, GB, Marino, A. Chesson, A and Struve, F (1992): Electrical states in the rabbit brain can be altered by light and electromagnetic fields. Brain Res 570:307-315.

Canady, DJ and Lee, RC (1991): Scientific basis for clinical applications of electric fields in soft tissue repair, in Electromagnetics in Medicine and Biology, Brighton, C T and Pollack, SR (eds.). San Francisco: San Francisco Press, 275-280.

Carson, JJL, Prato, FS, Drost, DJ, Diesbourg, LD and Dixon, SJ (1990): Time-varying magnetic fields increase cytosolic free $Ca^2$ in H-60 cells. Am J Physiol Soc 259 (Cell Physiol 28): C687-C692.

Fleischmann, A, Prolov, K, Abarbanel, J and Belmaker, RH (1995): The effect of transcranial magnetic stimulation of rat brain on behavioral models of depression. Brain Res 699:130-132.

Frey, A.H. (ed.) (1994): On the Nature of Electromagnetic Field Interactions with Biological Systems, R.G. Landes Co., Austin, Texas.

Fuller, M, Dobson, J, Wieser, HG and Moser, S (1995): On the sensitivity of the human brain to magnetic fields: Evocation of epileptiform activity. Brain Res Bull 36:155-169.

Grisaru, N, Yaroslavsky, U, Abarbanel, J, Lambert, T and Belmaker, RH (1994): Transcranial magnetic stimulation in depression and schizophrenia. Eur Neuropsychopharmacol 4:287-288.

Holden, C (1995): Substitute for shock therapy? Science 1/DEC, 270, 5241:1443.

Ito, H and Bassett, Cal (1983): Effect of weak, pulsing electromagnetic fields on neural regeneration in the rat. Clin Orthopaed 181:283-290.

Kavaliers, M and Ossenkopp, K-P (1985): Exposure to rotating magnetic fields alters morphine-induced behavioral responses in two strains of mice. Neuropharmacol 24:4:337-340.

Kavaliers, M and Ossenkopp, K-P (1986): Magnetic fields differentially inhibit mu, delta, kappa and sigma opiate-induced analgesia in mice. Peptides 7: 449-453.

Kavaliers, M and Ossenkopp, K-P (1986b): Stress-induced opioid analgaesia and activity in mice: Inhibitory influences of exposure to magnetic fields. Psychopharmacol 89:440-443.

Kavaliers, M and Ossenkopp, K-P (1986): Magnetic field inhibition of morphine-induced analgesia and behavioral activity in mice: Evidence for involvement of calcium ions. Brain Res 379:30-38.

Kavaliers, M and Ossenkopp, K-P (1987): Calcium channel involvement in magnetic field inhibition of morphine-induced analgesia. Naunyn-Schmiedeberg's Arch Pharmacol 336:308-315.

Kavaliers, M and Ossenkopp, K-P (1988): Magnetic fields inhibit opioid-mediated "analgesic" behaviours of the terrestrial snail, *Cepaea nemoralis*. J Comp Physiol A 162:551-558.

Kavaliers, M, Ossenkopp, K-P and Hirst, M (1984): Magnetic fields abolish the enhanced nocturnal analgesic response to morphine in mice. Physiol Behav 32:261-264.

Kavaliers, M, Ossenkopp, K-P and Tysdale, DM (1991): Evidence for the involvement of protein kinase C in the modulation of morphine-induced "analgesia" and the inhibitory effects of exposure to 60-Hz magnetic fields in the snail, *Cepaea nemoralis*. Brain Res 554: 65-71.

Kwong-Hing, A, Sandhu, HS, Prato, FS, Frappier, JRH and Kavaliers, M (1989): Effects of magnetic resonance imaging (MRI) on the formulation of mouse dentin and bone. J Exper Zool 252:53-59.

Lerchl, A, Honaka, Ko and Reiter, RJ (1991): Pineal gland "magnetosensitivity" to static magnetic fields is a consequence of induced electric currents (eddy currents). J Pineal Res 10:109-116.

Lindstrom, E, Lindstrom, P, Berglund, A, Mild, KH and Lundgren, E (1993): Intracellular calcium oscillations induced in a T-cell line by a weak 50 Hz magnetic field. J Cell Physiol 156:395-398.

Lohmann, KJ and Willows, AOD (1991): An identifiable molluscan neuron responds to changes in earth-strength magnetic fields. J exp Biol 161:1-24.

Lyskov, E, Juutilainen, J, Jousmaki, V, Hänninen, O, Medvedev, S and Partamem, J (1993): Influence of short-term exposure of magnetic field on the bioelectrical processes of the brain and performance. Intern J Psychophysiol 14:227-231.

Mather, JG and Baker, RR (1981): Magnetic sense of direction in woodmice for route-based navigation. Nature 291:152-155.

Ossenkopp, K-P and Kavaliers, M (1987): Morphine-induced analgesia and exposure to low-intensity 60-Hz magnetic fields: inhibition of nocturnal analgesia in mice is a function of magnetic field intensity. Brain Res 418:356-360.

Ossenkopp, K-P and Cain, DP (1988): Inhibitory effects of acute exposure to low-intensity 60-Hz magnetic fields on electrically kindled seizures in rats. Brain Res 442:255-260.

Winston, C, Parris, V, Janicki, PK, Johnson, BW, Jr., and Matthews, L (1994): The behavioral and biochemical effect of pulsating magnetic field treatment (PMFT) on chronic pain produced by chronic constriction injury of sciatic nerve in rat. Analgesia 1:1:57-64.

Pascual-Leone, A, Valls-Solé, J, Brasil-Netoo, JP Cammarota, A, Grafman, J and Hallett, M (1994): Akinesia in Parkinson's Disease. II. Effects of subthreshold repetitive transcranial motor cortex stimulation. Neurology 44:892-898.

Phillips, JB and Borland, SC (1992): Behavioural evidence for the use of a light-dependent magnetoreception mechanisms by a vertebrate. Nature 359:142-144.

Phillips, JB and Sayeed, O (1993): Wavelength-dependent effects of light on magnetic compass orientation in *Drosophila melanogaster*. J Comp Physiol A 172: 303-308.

Prato, FS, Frappier, JRH, Shivers, RR, Kavaliers, M, Zabel, P, Drost, D and Lee, T-Y (1990): Magnetic resonance imaging increases the blood-brain barrier permeability to 153-gadolinium diethylenetriaminepentaacetic acid in rats. Brain Res 523:301-304.

Prato, FS, Wills, JM, Frappier, JRH, Drost, DJ, Lee, T-Y, Shivers, RR and Zabel, P (1994): Blood-brain barrier permeability in rats is altered by exposure to magnetic fields associated with magnetic resonance imaging at 1.5T. Microscopy Research and Technique 27:528-534.

Reiter, RJ (1992): Alterations of the circadian melatonin rhythm by the electromagnetic spectrum: A study in environmental toxicology. Reg Toxicol Pharmacol 15:226-244.

Reiter, RJ and Richardson, BA (1992): Magnetic field effects on pineal indoleamine metabolism and possible biological consequences. FASEB J 6:2283-2287.

Schneider, T, Thalau, H-P and SEmm, P (1994): Effects of light or different earth-strength magnetic fields on the nocturnal melatonin concentration in a migratory bird. Neurosci Lett 168:73-75.

Selmaoui, B and Touitou, Y (1995): Sinusoidal 50Hz magnetic fields depress rat pineal NAT activity and serum melatonin: Role of duration and intensity of exposure. Life Sci 57:14:1351-1358.

Semm, P and Beason, RC (1990): Responses to small magnetic variations by the trigeminal system of the bobolink. Brain Res Bull 25:735-740.

Semm, P, Schneider, T and Vollrath, L (1980): Effects of an earth-strength magnetic field on electrical activity of pineal cells. Nature 288:607-608.

Shivers, RR, Kavaliers, M, Teskey, GC, Prato, FS and Pelletier, R-M (1987): Magnetic resonance imaging temporarily alters blood-brain barrier permeability in the rat. Neurosci Lett 76:25-31.

Sisken, BF, Kanje, J, Lundborg, G and Kurtz, W (1990): Pulsed electromagnetic fields stimulate nerve regeneration in vitro and in vivo. Restor Neurol Neurosci 1:303-309.

Steffensen, B, Caffesse, RG, Hanks, CT, Avery, JK and Wright, N (1988): Clinical effects of electromagnetic stimulation as an adjunct to periodontal therapy. J Periodontol JAN/88 59:1:46-52.

Teskey, GC, Prato, FS, Ossenkopp, K-P and Kavaliers, M (1988): Exposure to time varying magnetic fields associated with magnetic resonance imaging reduces fentanyl-induced analgesia in mice. Bioelectromagnetics 9:2:167-174.

Thomas, AW, Kavaliers, M and Prato, FS (1996): Antinociception ("analgesia") induced by weak extremely low frequency complex neuroelectro-magnetic pulses. Bioelectromagnetics Soc Abstracts 18, in press.

Thomas, AW, Kavaliers, M and Prato, FS (1996): Development of tolerance to the opioid-mediated antinociceptive effects of weak extremely low frequency complex neuroelectromagnetic pulses. Bioelectromagnetics Soc Abstracts 18, in press.

Walleczek, J (1992): Electromagnetic field effects on cells of the immune system: The role of calcium signalling, FASEB J 6:3177-3185.

Walleczek, J and Liburdy, RP (1990): Nonthermal 60 Hz sinusoidal magnetic-field exposure enhances $^{45}Ca^{2+}$ uptake in rat thymocytes: dependence on mitogen activation. FEBS 271:1,2:157-160.

Zyss, T (1994): Deep magnetic brain stimulation—The end of psychiatric electroshock therapy? Medical Hypotheses 43: 69-74.

Persinger, MA, Koren, SA, Makarec, K, Richards, P and Youlton, S (1991): Differential effects of wave form and the subject's possible temporal lobe signs upon experiences during cerebral exposure to weak intensity magnetic fields. J Bioelectricity 10(1&2):141-184.

Richards, PM, Persinger, MA and Koren, SA (1993): Modification of activation and evaluation properties of narratives by weak complex magnetic field patterns that simulate limbic burst firing. Intern J Neurosci 71:71-85.

Gillis, C and Persinger, MA (1993): Shifts in the Plutchik emotion profile indices following three weekly treatments with pulsed vs continuous cerebral magnetic fields. Perceptual and Motor Skills 76:168-170.

Tiller, SG and Persinger, MA (1994): Enhanced hypnotizability by cerebrally applied magnetic fields depends upon the order of hemispheric presentation: An anisotropic effect. Intern J Neurosci 79:157-163.

Persinger, MA, Richards, PM and Koren, SA (1994): Differential ratings of pleasantness following right and left hemispheric application of low energy magnetic fields that stimulate long-term potentiation. Intern J Neurosci 79:191-197.

Bureau, YRJ and Persinger, MA (1995): Decreased incidence of limbic motor seizures following twenty pairings of subclinical lithium-pilocarpine and a complex "burst-firing" magnetic field. Electro- and Magnetobiology 14(1):1-6.

Persinger, MA, Ludwig, HW And Ossenkopp, K-P (1973): Psychophysiological effects of extremely low frequency electromagnetic fields: a review. Perceptual and Motor Skills, Monograph Supplement 3-V36.

Persinger, MA (1988): The Modern Magnetotherapies, in Marino, AA (ed.) Modern Bioelectricity, NY, Dekker:589-627.

Persinger, MA (1995): On the possibility of directly accessing every human brain by electromagnetic induction of fundamental algorithms. Perceptual and Motor Skills 80:791-799.

Adey, WR (1973): The influences of impressed electrical fields at EEG frequencies on brain and behavior. Behavior and Brain Electrical Activity, Burch, [ ]and Alshuler, [ ], eds., NY, Plenum: 363-390.

Fleming, JL, Persinger, MA and Koren, SA (1994): Magnetic pulses elevate nociceptive thresholds: comparisons with opiate receptor compounds in normal and seizure-induced brain-damaged rats. Electro- and magnetobiology 13(1):67-75.

* cited by examiner

Table of Romberg Quotients
(Mean ± 1 S.E.M.)

$$RQ_{Measure} = \frac{EyesClosed_{Measure}}{EyesOpen_{Measure}}$$

| | 0.12 W/m² | | 0.51 W/m² | |
|---|---|---|---|---|
| Light Intensity : | | | | |
| Exposure : | Sham | PEMF | Sham | PEMF |
| Measure | | | | |
| Line : | 1.29 ±0.14 | 1.78 ±0.24* | 1.26 ±0.08 | 1.14 ±0.05* |
| Area : | 1.78 ±0.37 | 3.79 ±0.92* | 1.78 ±0.21 | 1.44 ±0.12* |
| Path : | 1.64 ±0.14 | 1.88 ±0.24 | 1.66 ±0.10 | 1.69 ±0.13 |

\* Significantly different between Light Intensities
The interaction of Light Intensity and Exposure is significant (i.e. Line... $F_{1,33}$=11.8, P < 0.003).

FIGURE 12

|  | Pre-experiment, Mean (Std Dev) | | Post-experiment, Mean (Std Dev) | |
| --- | --- | --- | --- | --- |
|  | RA | FM | RA | FM |
| Binary Question (No = 0, Yes = 1) | | | | |
| Do you have pain in your shoulders, arms or hands? | 0.80 (0.41) | 0.86 (0.36) | 0.60 (0.51) | 0.86 (0.36) |
| Do you have pain in your hips, legs or feet? | 0.80 (0.41) | 1.00 (0.00) | 0.67 (0.49) | 0.86 (0.36) |
| Do you have pain in your neck? | 0.47 (0.52) | 0.86 (0.36) ^ | 0.33 (0.49) | 0.79 (0.43) ^ |
| Do you pain in your back? | 0.33 (0.49) | 0.93 (0.27) ^ | 0.33 (0.49) | 0.86 (0.36) ^ |
| Do you have pain elsewhere? | 0.40 (0.51) | 0.57 (0.51) | 0.40 (0.51) | 0.57 (0.51) |
| Analog Pain Scale (10 cm line) 0 = None, 10 = Very. | | | | |
| How bad is your pain RIGHT NOW? | 3.34 (2.09) ↑ | 4.96 (1.94) ^↑ | 2.87 (2.09) | 4.55 (2.50) |
| How bad is your stiffness RIGHT NOW? | 3.13 (2.77) | 4.36 (2.54) | 2.50 (1.44) | 4.28 (2.82) ^ |
| How tired or fatigued are you RIGHT NOW? | 4.26 (2.91) ↑ | 5.32 (2.75) ↑ | 2.99 (2.03) | 4.56 (2.68) |
| How weak do you feel RIGHT NOW? | 2.67 (1.90) | 3.79 (2.40) | 2.78 (2.50) | 3.09 (2.67) |
| How tense, nervous or anxious do you feel RIGHT NOW? | 1.80 (2.06) ↑ | 2.64 (2.16) ↑ | 1.63 (1.63) | 1.77 (1.51) |
| How dizzy do you feel RIGHT NOW? | 2.14 (2.50) | 1.88 (1.93) | 1.94 (1.76) | 1.66 (1.62) |

^ relates to a significant difference (greater than, $P < 0.05$) between RA and FM within Pre- or Post-experiment testing.

↑ relates to a significant difference (greater than, $P < 0.05$) between Pre- and Post-experiment testing.

FIGURE 13

Table of Results
(Mean ± 1 S.E.M.)

$$RQ_{Measure} = \frac{EyesClosed_{Measure}}{EyesOpen_{Measure}}$$

Light Intensity:     0.12 W/m$^2$                    0.51 W/m$^2$
Exposure     :   Sham      PEMF           Sham      PEMF
Measure (Romberg Quotient, RQ)
    Line  :   1.29 ±0.14  1.78 ±0.24*    1.26 ±0.08  1.14 ±0.05*
    Path  :   1.64 ±0.14  1.88 ±0.24     1.66 ±0.10  1.69 ±0.13

\* Significantly different between Light Intensities
The interaction of Light Intensity and Exposure is
SIGNIFICANT (LINE: $F_{1,33} = 11.8$, $p < 0.002$).

Direction Sensitivity (Mean Axis Shift Difference (m), PEMF-Sham)

Light Intensity:      0.12 W/m$^2$                  0.51 W/m$^2$
    X axis : EO 4.805E-04±1.69E-03       9.517E-04±6.45E-03
            EC 2.154E-05±3.06E-03       1.915E-03±7.22E-04*
    Y axis : EO 5.670E-04±1.25E-03       1.242E-03±6.68E-04
            EC 2.532E-04±1.60E-03       1.903E-04±8.40E-04

\* Significantly different between Exposure condition only.
The interaction of Light Intensity and Exposure is not significant (P > 0.65).

DIAGNOSIS AND CLASSIFICATION OF DISEASE AND DISABILITY USING LOW FREQUENCY MAGNETIC FIELD DESIGNED PULSES (CNPS)

RELATED APPLICATIONS

This application is a continuation under 35 U.S.C. 111(a) of PCT/CA01/00828 filed Jun. 7, 2001 and published in English as WO 01/93948 A2 on Dec. 13, 2001, which claims priority from U.S. Provisional Patent Application Ser. No.: 60/209,994, filed Jun. 8, 2000, which application and publication are incorporated herein by reference.

FIELD OF INVENTION

The invention relates to magnetic fields and in particular, to the use of magnetic fields for the diagnosis and classification of disease in both human and veterinarian medicine.

BACKGROUND OF THE INVENTION

Studies have suggested that magnetic stimuli can affect behavioral, cellular and physiological functions of animals. As a result magnetic therapy was developed for the therapeutic treatment of pain in humans as well as for the general well-being of humans.

Simple pulsed magnetic fields with very high time changing magnetic fields (10,000 Tesla/s) (Barker et al., 1987) have been used for the stimulation of nerves (depolarisation and induction of action potential) and for the treatment of primarily affective disorders. These pulses are, in general, simple unipolar or bipolar pulses which are designed to induce currents in nerves and, in themselves, do not carry information as a function of time within each pulse sequence nor can the pulses be used for any diagnostic classification.

UK Patent Application 2 270 000 discloses a magnetic field induction therapy apparatus for the therapeutic treatment of pain and the alleviation of circulatory and respiratory problems.

U.S. Pat. No. 3,678,337 discloses an apparatus to be used indoors to generate magnetic fields to stimulate natural displacement currents in humans and thus generate general beneficial effects in such humans.

U.S. Pat. No. 5,066,272 discloses the use of magnetic pulses which are capable of inducing eddy currents in nearby brain tissue of sufficient strength and duration to cause tissue stimulation and disruption of high level cognitive function and, therefore, are useful in performing functional mapping of the brain. The pulses can also stimulate peripheral nerves and provide measurements of nerve conduction velocity for certain disease diagnosis or motor evoked potentials for surgical monitoring.

U.S. Pat. No. 5,935,054 discloses the use of weak externally applied magnetic fields for influencing the nervous system of a subject and in particular, as an aid to relaxation, sleep or arousal and clinically for the control of tremors, seizures and emotional disorders.

None of these prior art references, nor the literature in general, has contemplated or actually demonstrated that pulsed magnetic fields could be used for the diagnostic classification of disease, including diseases and health states associated with acute or chronic pain, fatigue or disability. Furthermore, none of the prior art has suggested or demonstrated the ability to separate patients into different disease categories based on exposure to pulsed magnetic fields.

It was previously demonstrated by the present Applicant in U.S. Pat. No. 6,234,953 (the entirety of which is hereby incorporated by reference) that specific low frequency pulsed magnetic fields (Cnps) having a plurality of intermittent waveforms could be used in methods for treating physiological, neurological and behavioral disorders. It is now unexpectedly demonstrated that such Cnps can be used for the diagnostic classification of disease.

SUMMARY OF THE INVENTION

The present invention provides methods of differential diagnoses of diseases in humans and animals which is rapid, safe, non-invasive, objective and well-tolerated. The methods of the invention result in a highly sensitive and specific classification of disease such as but not limited to diseases and health states associated with acute or chronic pain, fatigue or disability. The methods involve short duration exposures to relatively weak and safe magnetic fields (i.e. Cnps) to perturb human or animal cognition or physiological (below the limit of conscious sensory detection) responses. The physiological responses are measured either during the Cnp exposure or after the end of the exposure and represent the effects of this exposure. The physiological perturbation is then objectively and/or subjectively analyzed and used for the diagnostic classification of disease.

The Applicant has demonstrated that Cnps, generally applied or targeted to a specific body part or tissue of a subject, affect a physiological function. The change in the physiological function can then reliably be used to diagnose whether the subject is suffering from a disease condition. The change in the physiological function or functions can be assessed objectively and/or subjectively and still provide a diagnosis for a disease condition.

The method includes the design of a magnetic field (Cnps) which targets specific tissue by its specific waveform design. Localisation can also be enhanced by use of magnetic field generation devices which localise the patient's exposure in 3D space predominantly to target tissue. A whole-body exposure can still target the CNS rather than the peripheral nervous system if the Cnps pulse sequence (the variations in time of the magnetic field) has characteristics of the CNS rather than the peripheral nervous system.

The invention provides a method of disease diagnosis using specifically designed pulsed magnetic field (Cnps. such as those described in U.S. Pat. No. 6,234,953, the entirety of which is incorporated herein by reference). Furthermore, such Cnps may also be altered by the addition of ultra low frequency (near 0 to 0.1 Hz) components placed as time-varying periods spaced between repetitions of the pulse train. More particularly, the invention relates to the exposure of targeted tissue to Cnps and the assessment of the resulting perturbation of a measured selected physiological response. Differences in these measured physiological responses are subjectively and/or objectively used to determine patient pathology.

In accordance with an aspect of the present invention is the use of Cnps for the diagnosis of a disease condition in a subject.

In accordance with another aspect of the present invention is the use of Cnps in a method for the diagnosis of the severity of a disease condition in a subject. It is understood that the subject may be a human or animal subject.

In accordance with another aspect of the present invention is the use of Cnps in a method for the diagnosis of various disease conditions in humans or animals. The Cnps may be targeted to a specific tissue or body portion.

In accordance with still a further aspect of the present invention is the use of Cnps to affect a selected physiological function in a subject. The physiological function may be a motor or cognitive function.

In accordance with a further aspect of the present invention is a method for the diagnosis of disease conditions in a subject, the method comprising;

exposing a subject to a Cnps;

simultaneously monitoring a selected physiological function;

evaluating a change in the selected physiological function;

assessing said change in the selected physiological function; and classifying the subject into a disease category.

In accordance with another aspect of the present invention is a method for the diagnosis and assessment of disease conditions in a subject, the method comprising:

exposing a subject simultaneously to a selected Cnps and a first prescribed light intensity and frequency distribution while monitoring a selected physiological function;

exposing said subject a second time simultaneously to said selected Cnps and a different light intensity of the same or different frequency distribution as said first prescribed light intensity while monitoring a selected physiological function; and evaluating any change in the selected physiological function;

assessing said change in the selected physiological function; and classifying said subject into a disease category based on the assessment of the change in the selected physiological function.

In accordance with another aspect of the present invention is a method for the diagnosis and assessment of disease conditions in a subject, the method comprising;

exposing a subject to a first selected Cnps while monitoring a selected physiological function;

exposing said subject a second time to a second selected Cnps while monitoring a selected physiological function;

evaluating any change in the selected physiological function;

assessing said change in the selected physiological function; and classifying said subject into a disease category based on the assessment of the change in the selected physiological function.

In accordance with still another aspect of the present invention is a method for the diagnosis of disease conditions in a subject, the method comprising;

evaluating a selected physiological function in a subject;

exposing said subject to a selected Cnps;

evaluating any change in the selected physiological function;

assessing said change in the selected physiological function; and classifying said subject into a disease category based on the assessment of the change in the selected physiological function.

In accordance with another aspect of the present invention is a method for the diagnosis of disease conditions in a subject, the method comprising;

exposing a subject simultaneously to two or more selected Cnps while monitoring at least one selected physiological function;

evaluating any change in the at least one selected physiological function;

assessing said change in the at least one selected physiological function; and classifying said subject into a disease category based on the assessment of the change in the at least one selected physiological function.

The methods of the present invention may be used for the separation of patients with fibromyalgia and other acute and chronic central (neurogenic) pain states from those with rheumatoid arthritis and other acute and chronic peripheral (non-neurogenic) pain states. Various central disorders may also be diagnosed using the present method. Furthermore, the method may be used for the separation of patients with moderate to severe pain from those feigning pain; for separation of patients with moderate to severe fatigue from those feigning fatigue; and for separation of patients with moderate to severe disability related to pain and/or fatigue from those feigning disability. In general, the novel method allows for the assessment of the severity of certain disease conditions.

Physiological functions monitored in the method of the invention include but are not limited to standing balance, electrical activity in the brain, heart rate and rhythm, respiration, skin temperature, eye movements, cognition, memory, learning, vision or speech.

Subjective functions evaluated in the method of the invention include but are not limited to the extent of pain, extent of discomfort, extent of depression, extent of unpleasantness, extent of anxiety, extent of uneasiness, extent of excitement, extent of arousal, extent of attention and extent of suggestability. One skilled in the art would understand the scope and subjective functional assessment that can be effectively used in the methods of the present invention.

The method of the present invention also has utility for the determination of an objective measure of pain, fatigue and/or disability in a subject during normal activity or following exercise or repetitive tasks.

According to a further aspect of the present invention is a method of objectively measuring pain, fatigue and/or disability in a subject, the method comprising:

exposing a subject to a selected Cnps;

simultaneously monitoring a selected physiological function;

comparing the physiological function with that of a suitable control;

classifying the subject as experiencing pain, fatigue and/or a disability of feigning pain, fatigue and/or a disability.

According to a further aspect of the present invention is the use of Cnps for altering a physiological function in order to detect early stages of various disease conditions.

The method of the present invention serves as an objective assay leading to the separation of sub-classes of physical and behavioural pathologies in humans or animals.

In other aspects of the invention, the method can be used as a prognosis or predictive indicator of a change in a physical pathology in either humans or animals.

In yet another aspect of the present invention there is provided a system for the diagnosis of disease conditions in a subject, the system comprising;

a coil array that produces a uniform magnetic field that perturbs a physiological function in a subject that is quantitatively or qualitatively assessed to generate a data set;

a data set representing a control;
wherein the two data sets are comparatively analyzed to classify the subject in a disease category.

In yet another aspect of the invention there is provided a method for the diagnosis and assessment of disease conditions in a subject, the method comprising;
comparing a data set representing the perturbation of a physiological function in a subject with a data set representing a control;
classifying the subject in a disease category.

Other aspects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from the detailed description.

BRIEF DESCRIPTION OF THE DRAWINGS

The invention will now be described in relation to the drawings in which:

FIG. 12 sets forth Romberg Quotients.

FIG. 13 illustrates that the sway perturbing Cnps produces a different result when comparing rheumatoid arthritis (RA) patients to fibromyalgia (FM) patients for a subjective measure.

FIG. 14 summarizes results of responses under different light conditions to the same Cnps.

FIGS. 15A and 15B summarize the effects of the first magnetic field exposure on open field behavior.

FIGS. 16A and 16B summarize the effects of the second magnetic field exposure on open field behavior.

DETAILED DESCRIPTION OF THE PREFERRED EMBODIMENTS

It has now been demonstrated that designed Cnps can be used not only for therapeutic treatment of various clinical conditions, but now can also be used for the diagnosis and assessment of a variety of disease conditions some of which are related with pain and/or fatigue and may even be used to diagnose disability as a whole as well as the degree of disability. The use of weak magnetic field pulses to perturb a selected physiological function and recordation of the perturbation for analyses and subsequent disease assessment and diagnoses has not previously been done or suggested. This method has great clinical value in the accurate diagnosis of patients in order to provide for correct and expedient treatment. The present invention has value in the determination of "real pain" in a patient rather than "feigning pain". Both the medical community as a whole and health insurers may greatly benefit from such technology as it may save a tremendous amount of money that could be put to better use in providing health care to those genuinely in need.

The present invention may be used to diagnoses any type of disease state having an impact on motor or cognitive function such as for example but not limited to, Parkinson's, Huntington's chorea, Multiple Sclerosis (MS) and other central nervous system disorders. Peripheral disorders such as rheumatoid arthritis, those associated with diabetes and muscular dystrophy may also be diagnosed and assessed using the method of the present invention.

Patient Set-Up

Figure 1:
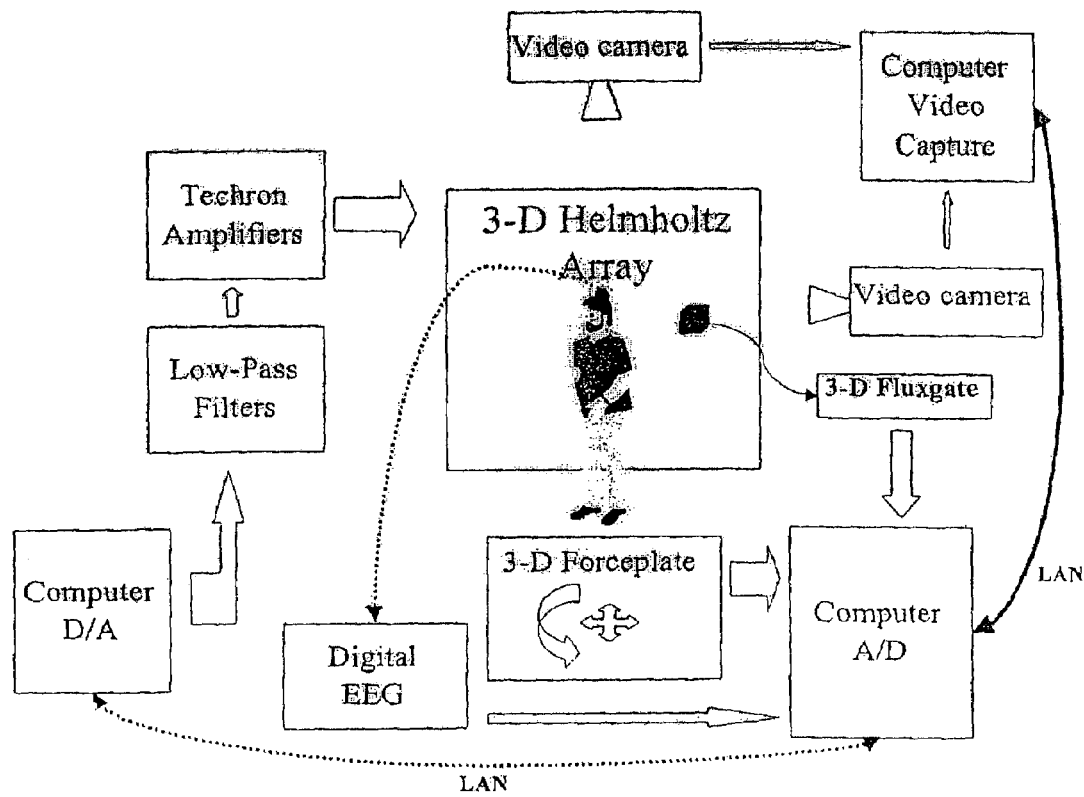
FIG. 1 illustrates a schematic diagram of the 3-D Helmholtz coil array magnetic field exposure and behavioral monitoring system.

The method of the present invention employs a 3-D Helmholtz coil array magnetic field exposure and behavioral monitoring system as is shown in FIG. 1. This system includes a forceplate, cameras and coil array housed in one room. Techron amplifiers and signal conditioners are housed in a separate but attached equipment closet and computers and control/monitoring equipment are housed in a separate but attached lab/office. It is understood that variations to the set up of this system can be made without affecting its integrity or functioning.

In the method of the present invention the patient is placed within a volume coil which produces a uniform magnetic field (Cnps) throughout a specified portion of the patient's anatomy, such as for example, the head. In the example shown in FIG. 2, the volume coil is sufficiently large that it exposes the entire patient's body to substantial magnetic fields. However, it is consistent with this amplification that smaller volume coils can be used which would encompass only the head or only a desired extremity. In the method of the invention, specifically designed magnetic field pulses are created such as those described in Applicant's U.S. Pat. No. 6,234,953.

Once the patient is placed in the volume coil, the patient is then connected to a physiological readout device. As shown in FIG. 1, this readout device is a 3D forceplate (OR6-7-1000, AMI, Watertown, Mass.). It is understood by those skilled in the art that other devices/methods could be just as effective and thus used as a readout device such as for example an EEG array, a SQUID array or a multi-lead ECG. The important feature for the selected readout device is that it be able to record a physiological phenomenon that is to be perturbed by the magnetic field exposure. For example, the 3D forceplate provides a measure of standing balance that is an outcome of the state of functioning of the vestibular system. If the vestibular system is negatively affected ("one gets dizzy"), standing balance deteriorates and the movement of the center of mass increases. In one embodiment of the present invention, the Cnps is designed to target the vestibular system and hence standing balance is the appropriate outcome measure (Thomas et al., 2001 a,b,c). In a further embodiment of the present invention, the target of the Cups is another system, such as the visual system and an outcome associated with vision is thus measured (Prato et al., 2001).

Magnetic Field Exposure

Figure 9:
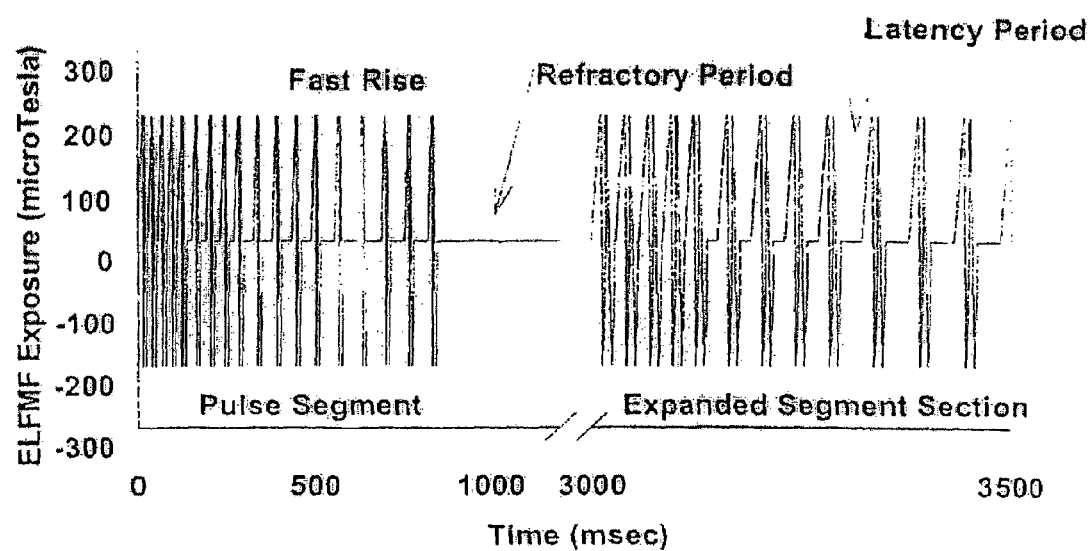
FIG. 9 shows that Cnps are modified to produce a 'pulse train' of Cnps spaced in time to alter the frequency spectra such that the effect of the general Cnps is to target the functioning of specific tissues in the organism. The rise time, latency period, refractory period, length of segment sections and number of repetitions per unit time are intrinsic to producing a specific Cnps action, such as altering the function of a specific tissue or group of tissues thus resulting in behavioral change in the organism. In this particular example, standing balance in human subjects was altered to highlight a difference in pain-related pathology, in that, rheumatoid arthritis sufferers differ statistically from fibromyalgia sufferers, and both clinical groups differ from normal controls.
Figure 10:
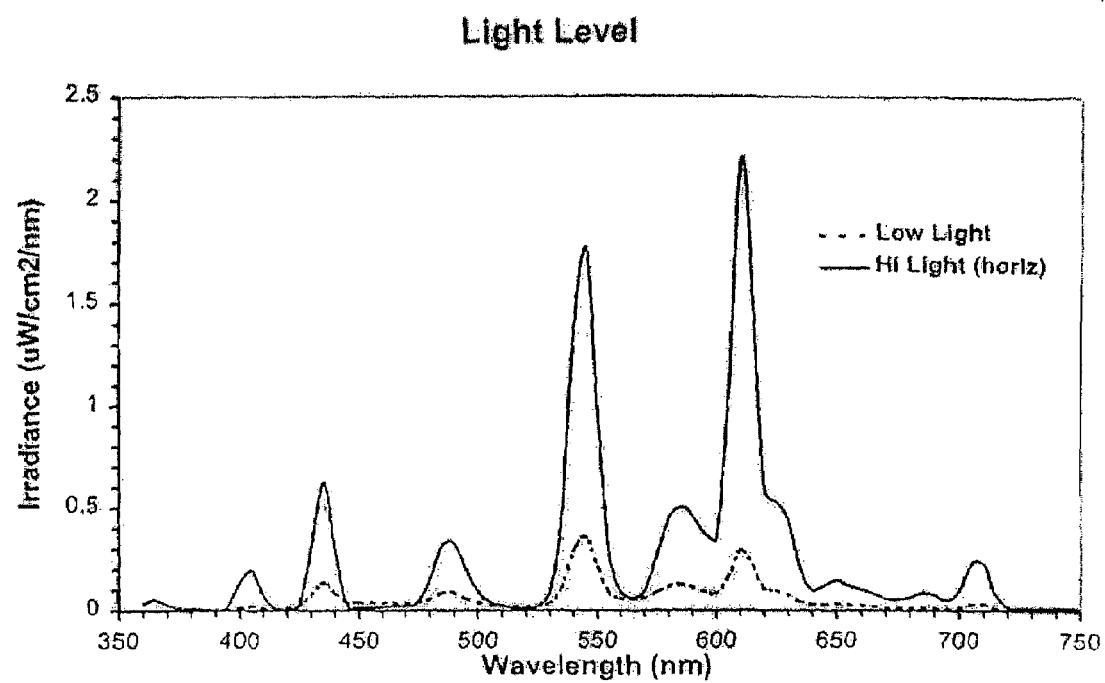
FIG. 10 is a graph illustrating real-time spectral analysis of the 'light level' conditions (high vs. low flourescent light levels) (McMahan LightSpex, N.C.). Light levels were recorded in a 'horizontal' attitude by pointing the recording device in the same direction as a subject's eye, from the same position in the apparatus or typical office working position.

Once a patient is set up within the system and a desired physiological function is selected for monitoring, the patient is then exposed to a desired Cnps. An example of the one used to target the vestibular system is shown in FIG. 9. It is not necessary and in fact it is preferred that a volume coil not touch the patient as magnetic fields can penetrate tissue without direct contact with the volume coil. It is also preferred that the magnetic field exposure be monitored to ensure that the prescribed pulsed magnetic field (Cnps) is actually produced by the volume coil (Thomas et al, 2001 a). In the example of the vestibular system, the exposure protocol has the subject standing on the forceplate in the centre of the exposure system such that the uniform magnetic field of the volume coil is centred at head level. It is preferred that subjects stand with their feet slightly apart (approximately 15 cm) in the centre of the 3D forceplate with all forceplate values continually digitally recorded at 10 samples per second throughout the randomly assigned four 2-minute exposures (see FIG. 9).

Using a standardised dialogue, subjects are asked to stand looking straight ahead with their eyes open and then be asked to slowly close their eyes, if required. Each of the trials (2 minute trial, eyes open/closed, sham/PEMF exposure) ends with a short rest period (approximate 30 s). At the end of each rest period (required for the operator to reset the data logger under computer control in a separate room and for the subject to relieve muscle tension), the next randomly assigned trial is initiated using the standardised dialogue. There should be no or minimal PEMF/sham-related cues in the apparatus (Thomas et al, 2000 a) thus ensuring the subject is blind to the exposure condition.

In a further aspect of the present invention, objective or subjective measures may be made after the end of exposure to the Cnps and compared to a baseline measurement made prior to exposure. In FIG. 13, it is demonstrated that the sway perturbing Cnps produces a different result when comparing rheumatoid arthritis (RA) patients to fibromyalgia (FM) patients for the subjective measure of "how bad is your pain RIGHT NOW?" and "how bad is your stiffness RIGHT NOW?"

Figure 11:
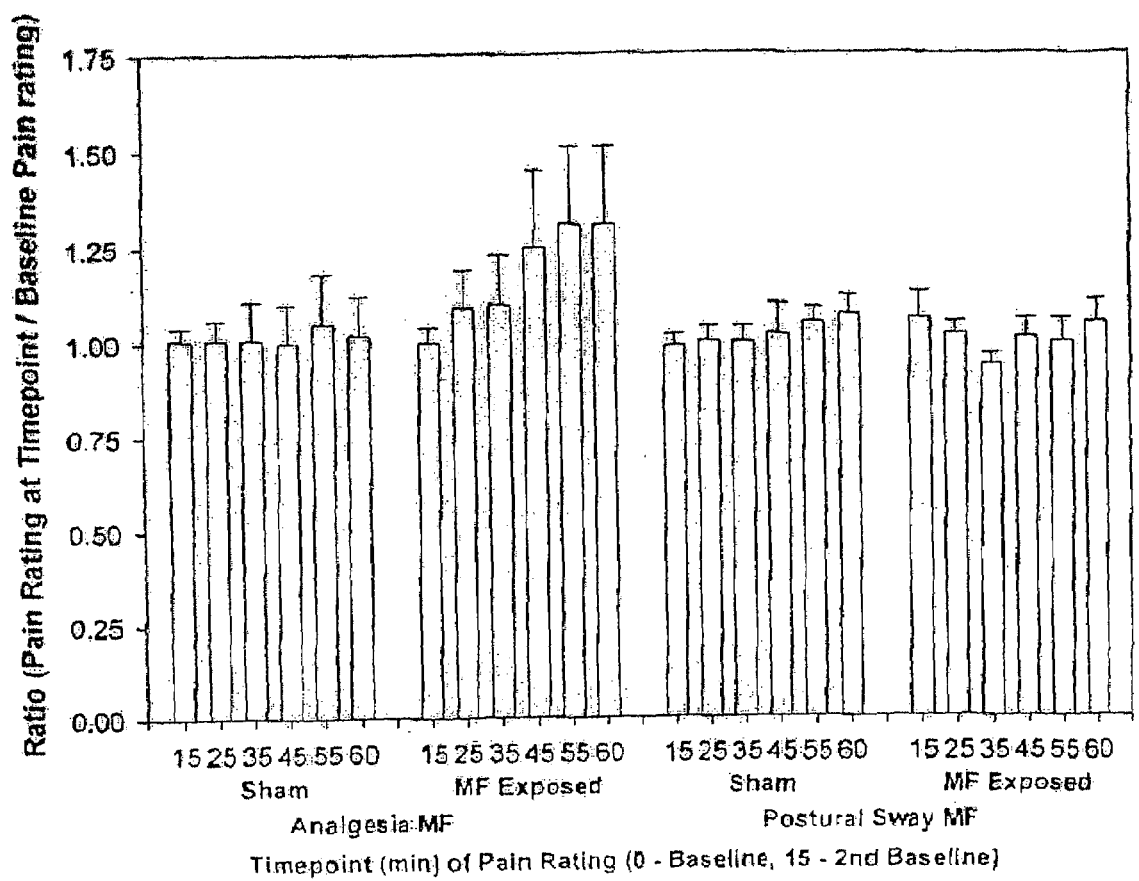
FIG. 11 is a graph illustrating the ratio of electric current (mA time point/mA baseline) applied to the web of the left thumb required to produce a subjective "moderate pain" rating in male and female university students (N=12) while exposed to either a sham or pulsed magnetic field.
Figure 15A:
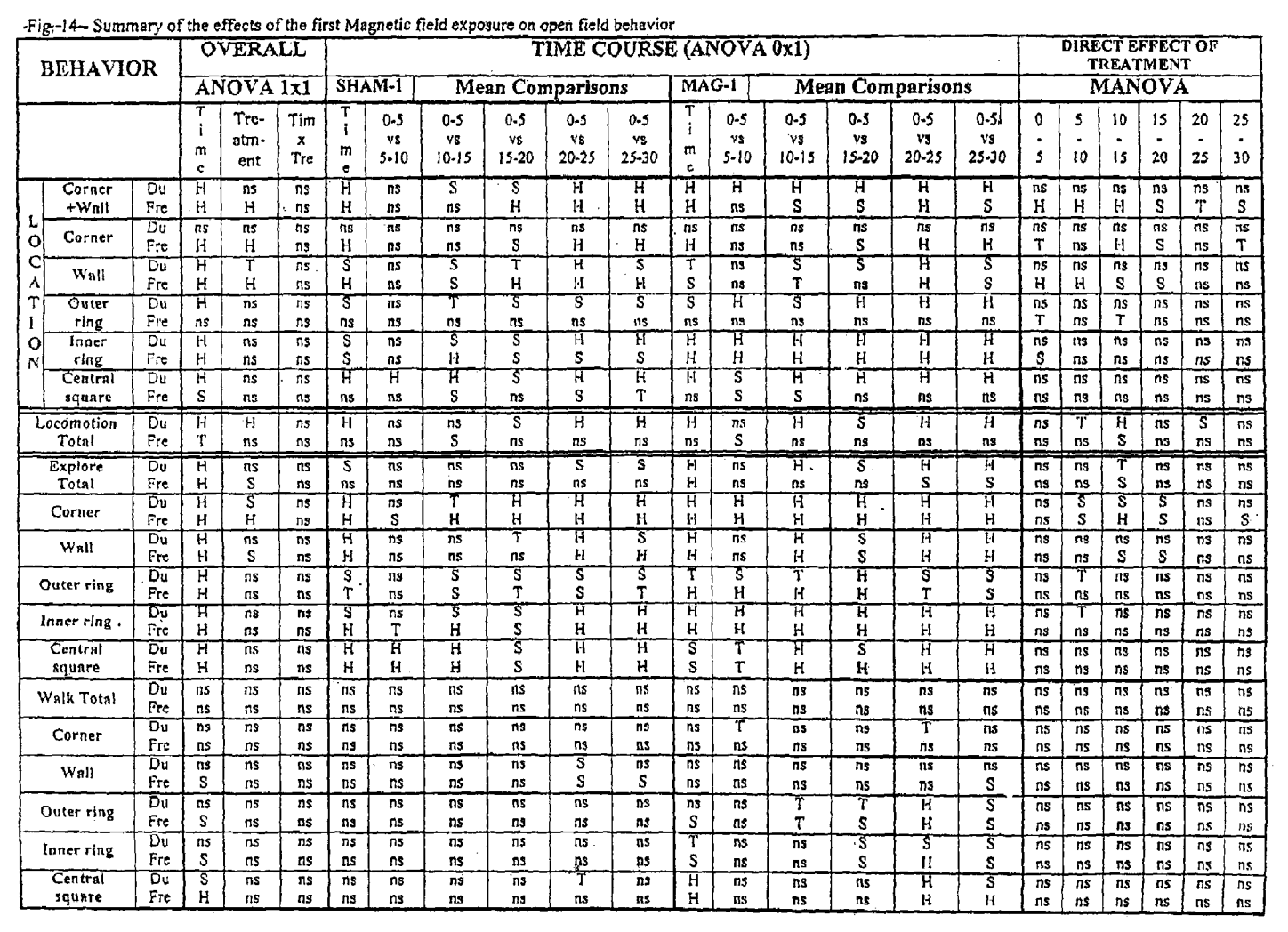
Figure 15B:
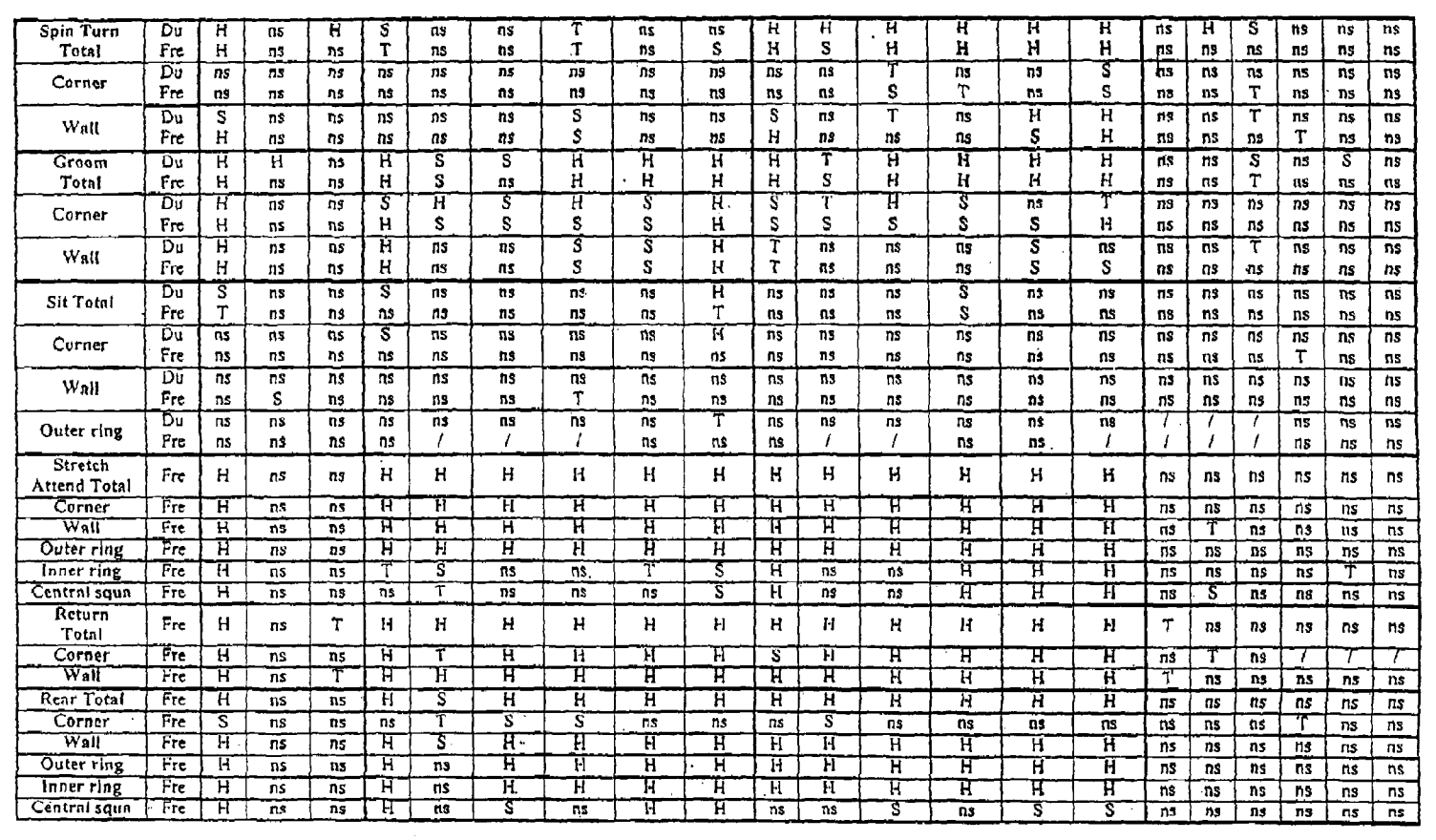
Figure 16A:
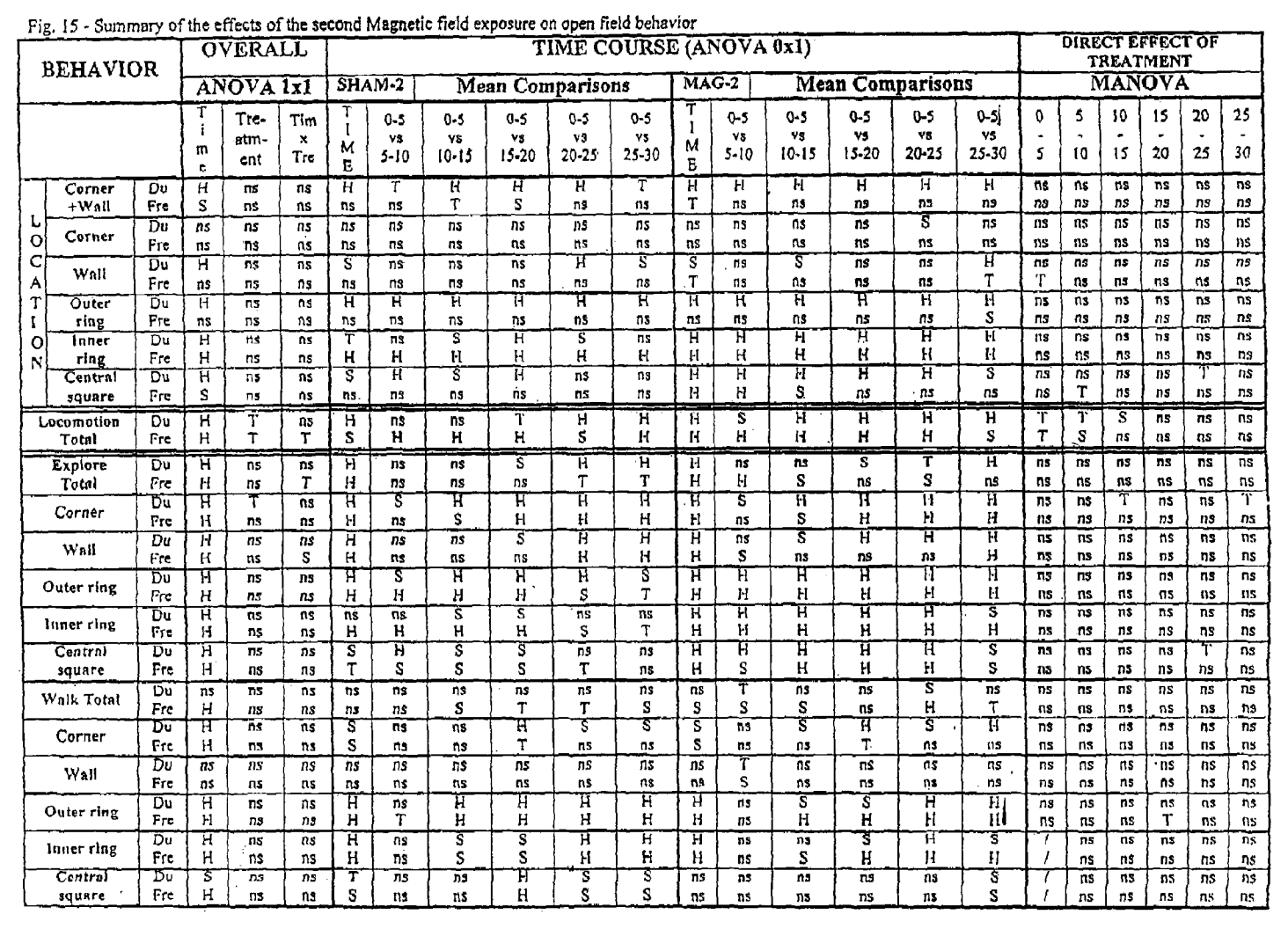
Figure 16B:
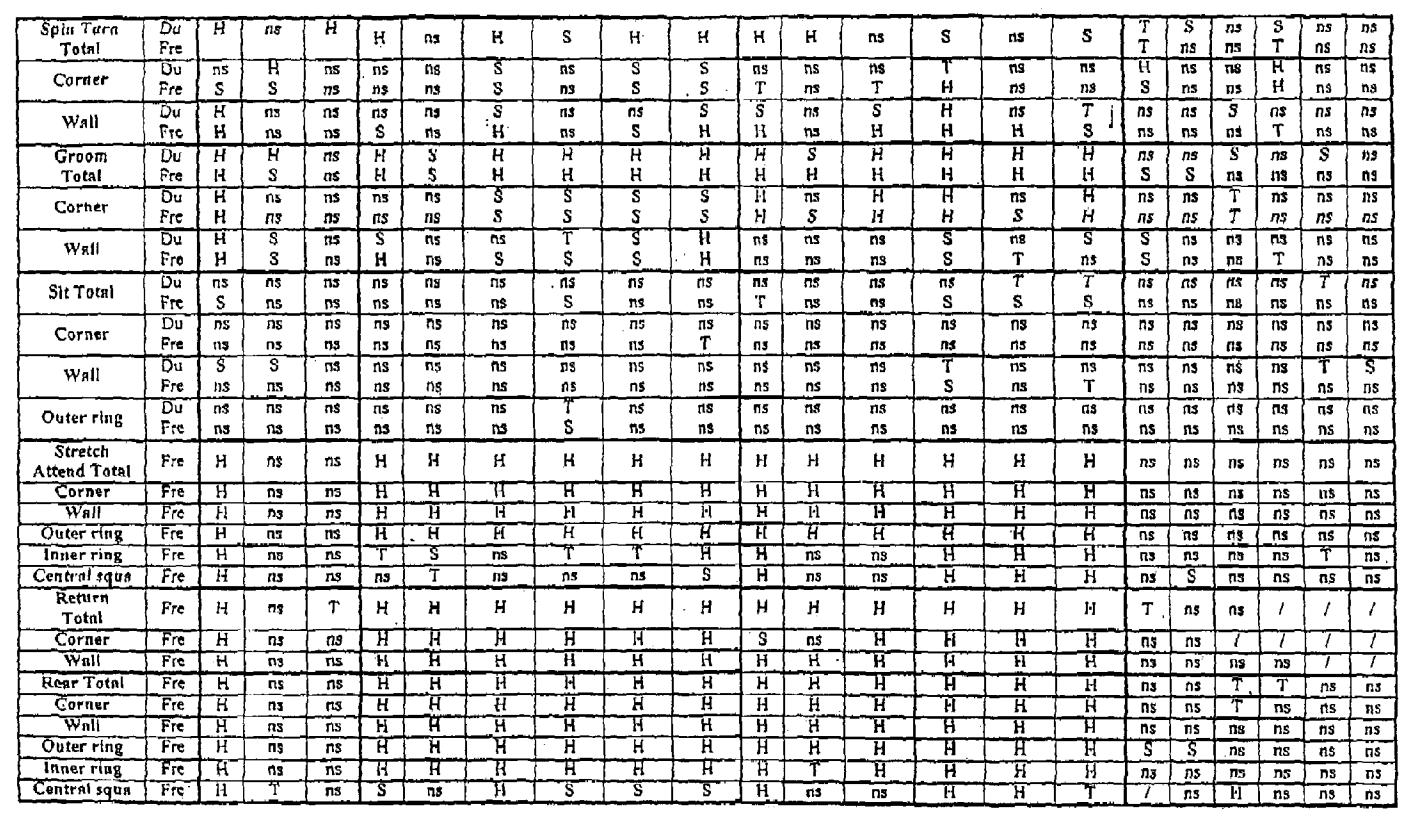

In still a further embodiment of the present invention the type of disease may be diagnosed and the severity of the disease diagnosed by comparing differential physiological effects from two different Cnps exposures. As seen in FIGS. 16A and 16B, in mice exposed to a postural sway altering Cnps results in different effects on different behaviours as compared to mice exposed to an analgesia-inducing Cnps as seen in FIGS. 15A and 15B, (Choleris et al., 2001). As seen in FIG. 11, differential physiological effects occur in normal human subjects when exposed to different Cnps and that for the same Cnps, human patients with different diseases respond differently. (Thomas et al., 2001c).

Figure 4:
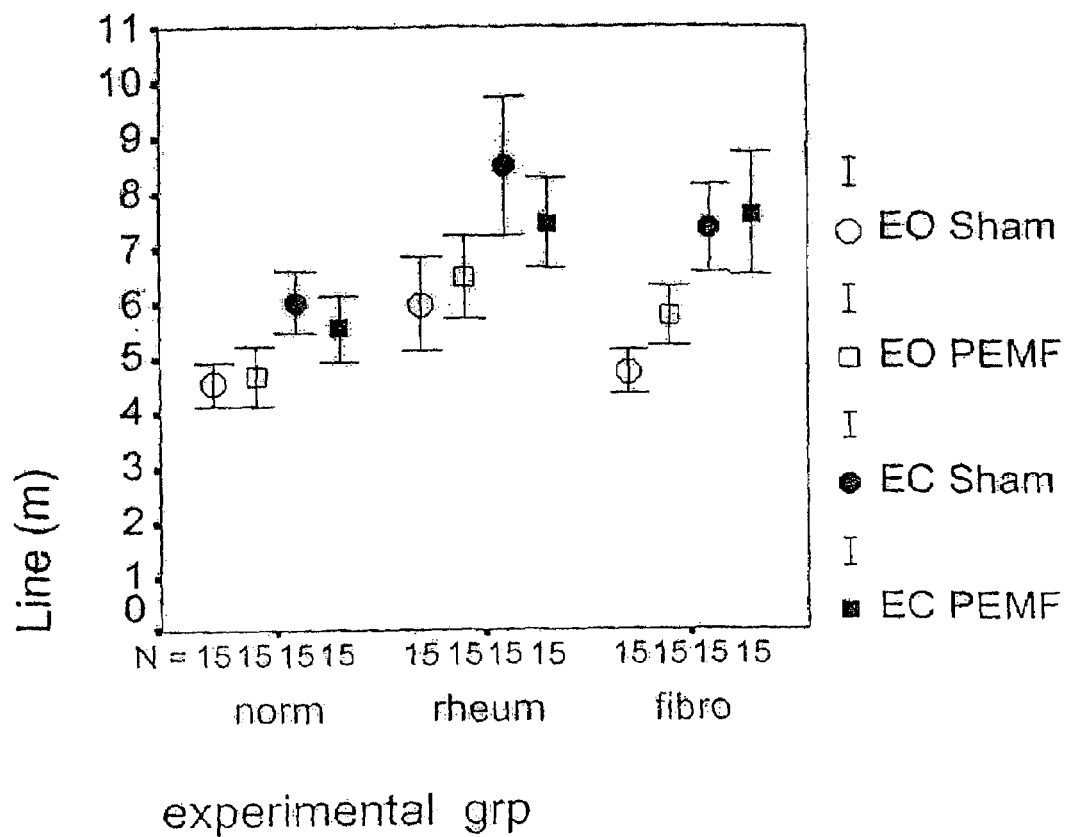
FIG. 4 shows a graph of Standing Balance Movement which represents an estimate of the cumulative amount of movement during normal standing. The center of pressure (COP) is projected vertically through the force plate, and the distance from the normalized center of standing pressure to each x-y coordinate (20 samples per second for each of the four 2 min trials) is summed to produce a 'Line' value in meters. With eyes open and during sham exposure, FM patients and controls appeared to have similar standing balance, with RA patients having decreased balance. With eyes closed, standing balance worsened from all three groups, but more for RA and FM patients than controls. Mixed design analysis of variance on the center of pressure (COP) movements show a significant interaction of eyes open/closed and sham/PEMF conditions [$F=8.78(1,42)$, $P<0.006$].
Figure 5:
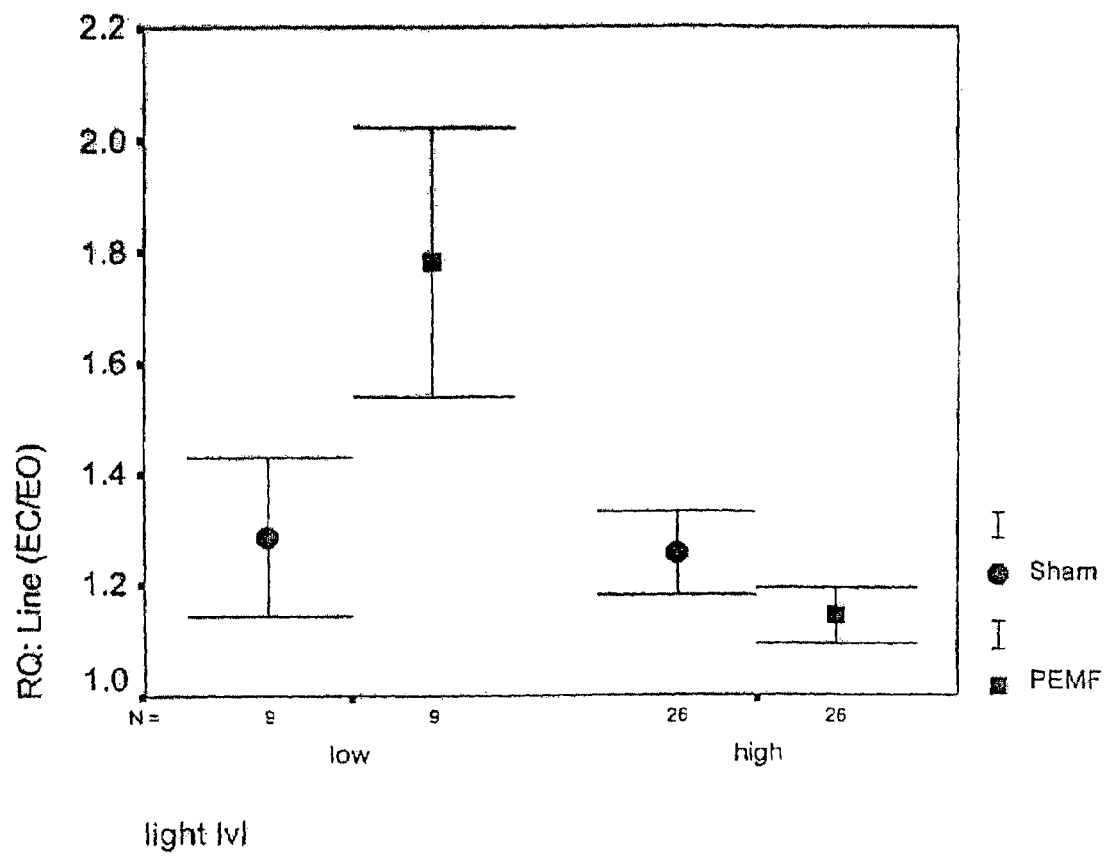
FIG. 5 shows a graph comparing the "Romberg Quotient (RQ)" (represents an estimate of the cumulative pattern of movement during normal standing balance (Sham vs PEMF exposed), with the 'eyes closed' condition divided by the 'eyes open' condition) in normals, fibromyalgia and rheumatoid arthritis patients. The center of pressure (COP) is projected vertically through the force plate, and the distance from the normalized center of standing balance of each x-y coordinate (20 samples per second for each of the four 2 min trials) is summed to produce a value in meters. The Romberg Quotient was highest amount FM patients. Romberg Quotients of COP movements improve significantly with PEMF exposure [$F=9.5(1,42)$, $P<0.005$].
Figure 6:
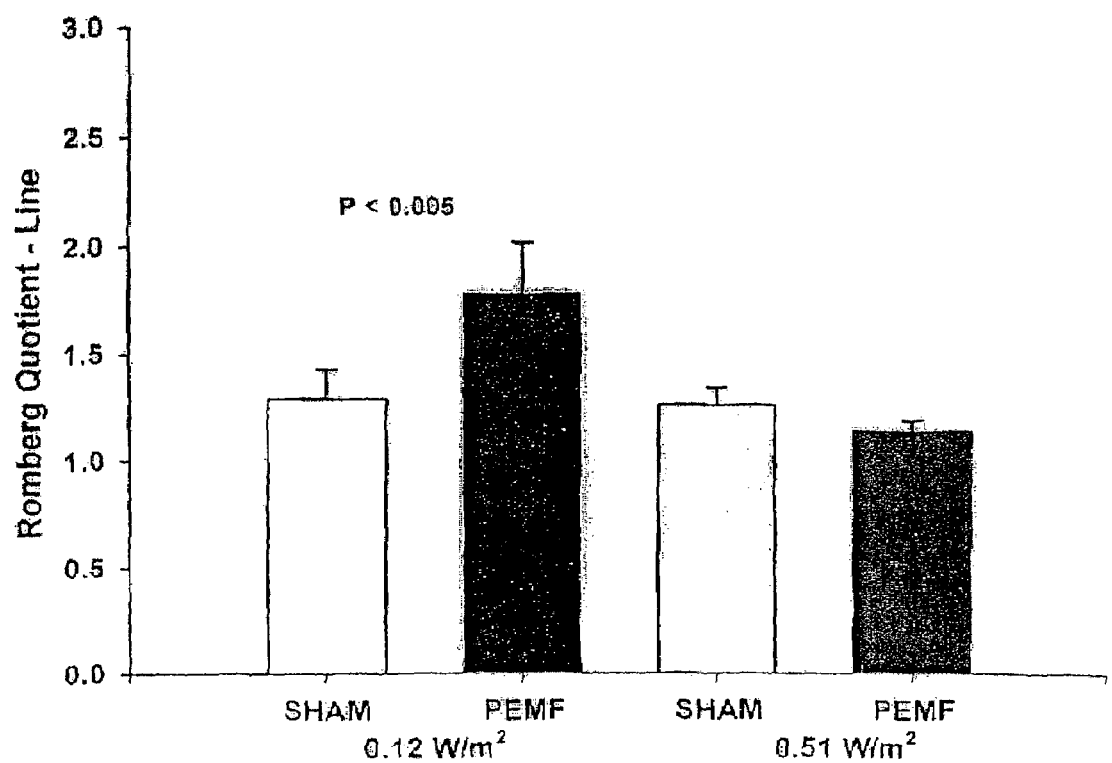
FIG. 6 is a graph illustrating the "Romberg Quotient (RQ)" representing a total distance of movement during normal standing balance (Sham vs PEMF exposed), with the 'eyes closed' condition divided by the 'eyes open' condition. The center of pressure (COP) is projected vertically through the force plate. This point is then traced to record the total length of the wandering path of movement around the normalized center of standing balance to each x-y coordinate (20 samples per second for each of the four 2 min trials) is summed to produce a 'Path length' in meters. COP path length shows an interaction approaching significance with clinical diagnosis [$F=3.2(1,28)$, $P<0.09$].

In yet a further embodiment of the present invention, the type of disease and severity of the disease may be diagnosed by comparing differential physiological effects from the same Cnps but under two different environmental conditions such as different light conditions. As seen in FIGS. 7A, 7B, 8A, 8B, 10 and in FIG. 14, there are different responses under different light conditions to the same Cnps (Prato et al., 2001). As seen in FIGS. 4, 5 and 6 there are different responses to the same Cnp in patients with different underlying diseases (Thomas et al., 2001c). Hence, diagnostic specificity and/or sensitivity should increase.

In yet a further embodiment of the invention, the type of and severity of the disease maybe diagnosed by comparing differential physiological effects from the same or different Cnps while being imaged with devices such as but not limited to functional magnetic resonance imaging (FMRI), position emission tomography (PET or SPECT), magnetoencephalography (MEG), electromyography (EMG) or electroencephalography EBG).

It is understood by those skilled in the art that other similar set ups are possible and within the scope of the invention. It is only important that the Cnps exposure be relatively short and that the outcome measure is made during or after the exposure and the measures are compared. If the outcome device itself is perturbed by the Cnps, then synchronisation of the measurements with the exposure is needed. For example, EEG and EMG measurements would use devices that would pick up signal from this Cnps. However, as the Cnps design has short latency and longer refractory periods, where the magnetic fields are zero, measurements could be made during these periods.

Analysis of Results

Outcome measures are then analysed in a manner relevant to the Cnps targeted tissue. In the example of the vestibular system, the measurements of the forceplate can be represented as a number of relevant parameters such as: total path, total area, total line and the total line can be broken down into the individual horizontal directions Table 1 and 3. FIG. 4 shows typical measures of line (in meters) for three groups of human subjects: normals, patients with rheumatoid arthritis (RA) and patients with fibromyalgia (FM). FIG. 5 shows how the outcome measures must be analysed such that the one sensitive to Cnps exposure is properly quantified. Here, the 'Romberg Quotient' shows that the vestibular system is perturbed by the PEMW but not the Sham exposure.

Classification of Patient Disease

The data is then appropriately analysed to separate patients into different disease categories dependent on how they responded to magnetic field exposure. Examination of FIG. 5 and FIG. 6 indicate that RA and FM differ in their response to Cnps and that each differ from the response of controls.

Patient Exposure Environment

Figure 7A:
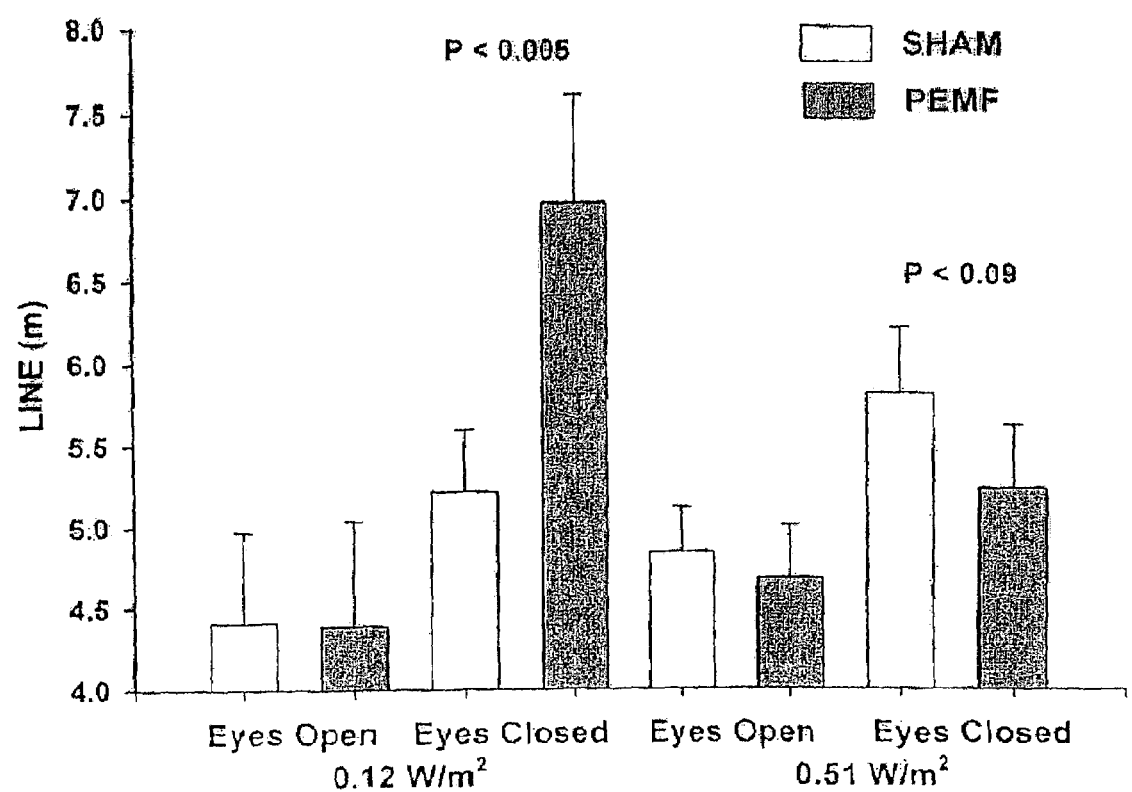
FIG. 7A is a graph illustrating a "Line" representing an estimate of the 'pattern' of movement during normal standing balance (Sham versus PEMF exposed) for subjects under two different light conditions. The center of Pressure (COP) is projected vertically through the force plate, and the distance from the normalized center of standing balance to each x-y coordinate (10 samples per second for each of the four 2 min trials) is summed to produce a 'Line' length value in meters.
Figure 7B:
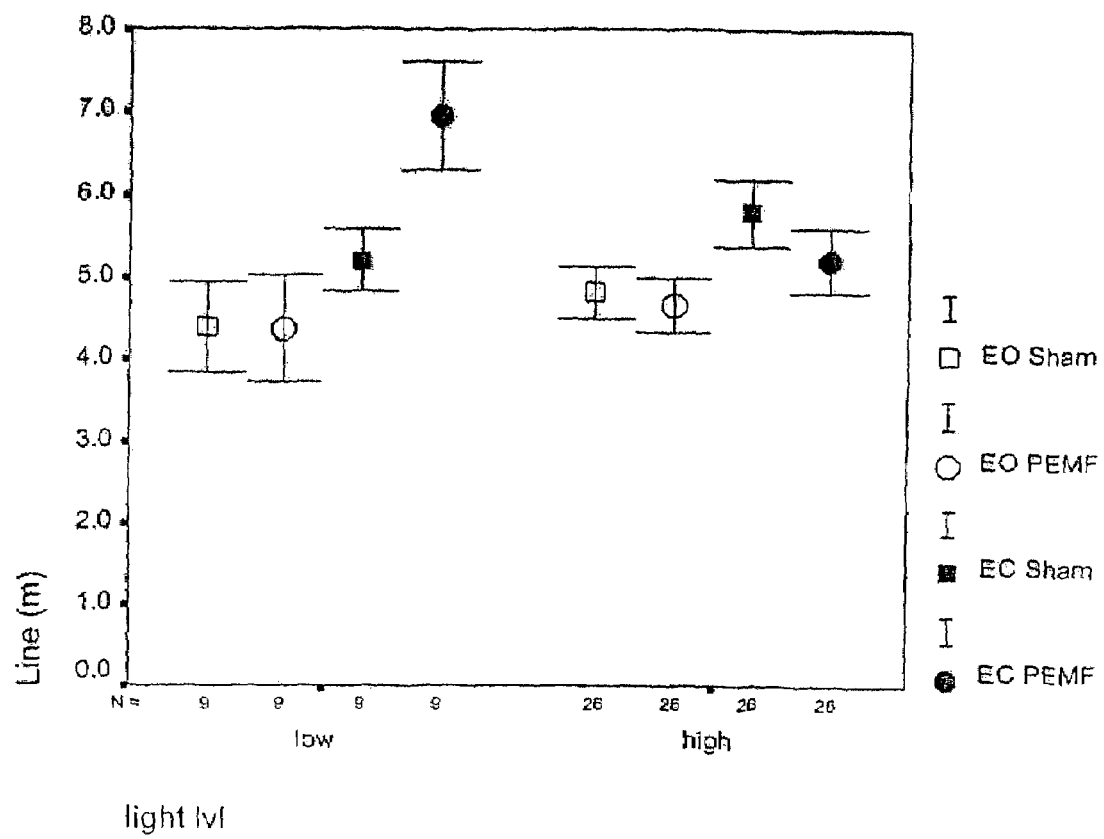
FIG. 7B is a graph illustrating a pattern of sway, as quantified using "line" (sum of line segment lengths) for subjects under two different light intensities, with eyes open and eyes closed, and sham exposed or PEMF exposed. Sway is increased with eyes closed and PEMF ($p<0.005$) under low light intensity ($0.12$ W/m$^2$) and decreased (approaching significance, $p<0.09$) under high intensity light ($0.51$ W/m$^2$).
Figure 8A:
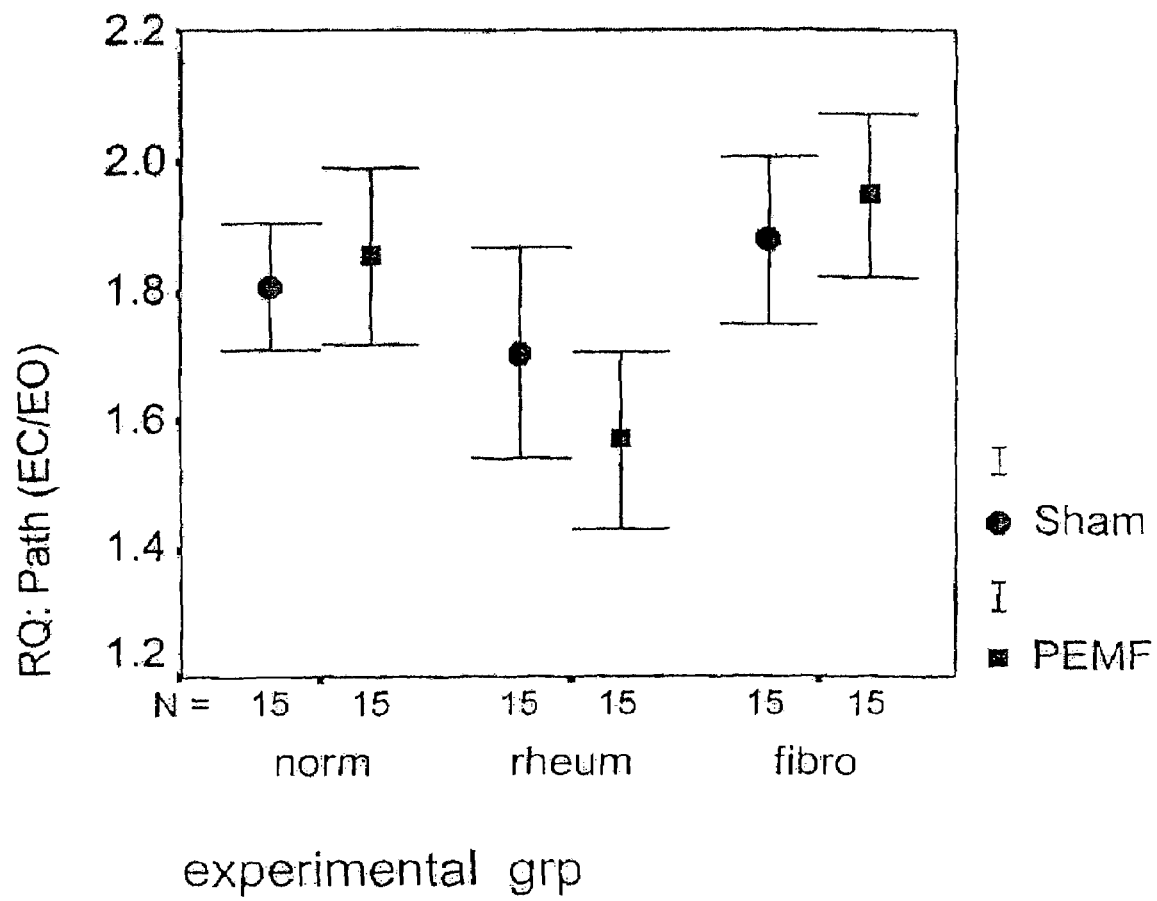
FIG. 8A is a graph illustrating the "Romberg Quotient (RQ)" which represents an estimate of the cumulative area of movement during normal standing balance (Sham versus PEMF exposed), with the 'eyes closed' condition divided by the 'eyes open' condition for subjects under two different light conditions. The center of pressure (COP) is projected vertically through the force plate and the pattern of movement around the normalized center of standing balance to each x-y coordinate (10 samples per second for each of the four 2 min trials) is summed to produce a value in meters.
Figure 8B:
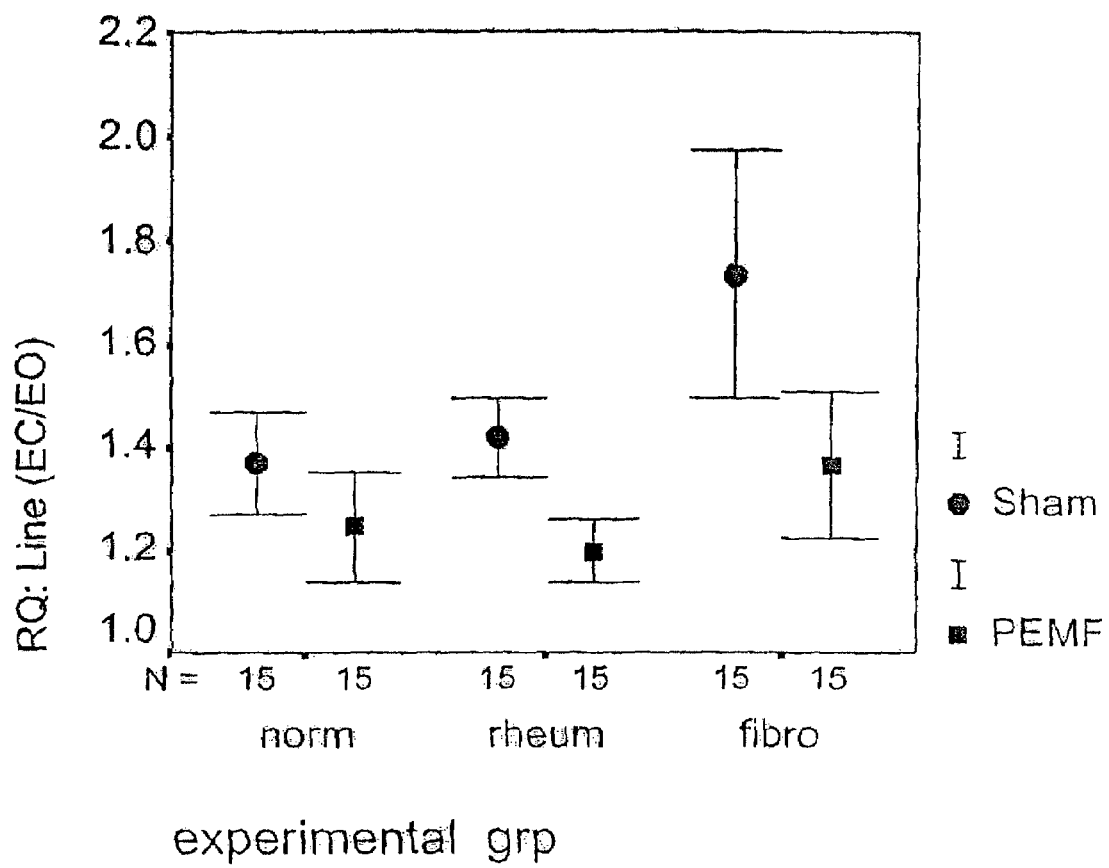
FIG. 8B is a graph illustrating the "Romberg Quotient (RQ)"+/−SEM (eyes closed/eyes open) indicating that the typical increase in movement which occurs when eyes are closed is similar for sham exposures under both light intensities. However, when exposed to PEMF's, the RQ significantly ($p<0.005$) increased under the low light ($0.12$ W/m$^2$) condition and was non-significant under the high light ($0.51$ W/m$^2$) condition.

Subjects under all embodiments are kept unaware of whether they are being exposed or sham exposed as placebo effects can be large in human subjects. Furthermore, exposure to other physical stimuli should be consistent for both sham and exposure. Particularly important is the exposure to light intensity. FIGS. 7A/B, 8A/B and 10 show the results from human subjects exposed to different light intensities. In the 9 normal subjects (mean age 26.4 (sd 2.6); 6 male, 3 female) exposed to a light intensity of 0.12 W/m$^2$, statistical analysis of the data (analysis of variance) indicated that there was a significant increase in standing movement during PEMP during eyes closed but not during eyes open. In a second experiment, 26 normal subjects (mean age 26.9 (sd 7.8); 13 male, 13 female) were exposed in an identical protocol except horizontal light levels were increased to 0.51 W/m$^2$ (350 Lux). For this second group, standing balance was improved during PEMF exposure while subject's eyes were closed, a finding contrary to that found at the lower light intensity.

It is clear from these results that the outcome measure from exposure to magnetic fields is affected by light intensity during that exposure, a result consistent with the literature on the effects of extremely low frequency magnetic fields on animal behaviour (Prato et al, 2000). This suggests that the preferred application of the method of the present invention may include control of light intensities during Cnps exposure. Further, that during single or multiple Cnps exposure monitoring differential light intensities may improve the sensitivity and specificity of disease differentiation.

The present invention has numerous applications in various industries where the determination and severity of true pain and general disability be identified.

EXAMPLES

The examples are described for the purposes of illustration and are not intended to limit the scope of the invention.

Methods involved in magnetic field generation referred to but not explicitly described in this disclosure and examples are reported in the scientific literature and are well known to those skilled in the art.

Example 1

Diagnostic Discrimination of Rheumatoid Arthritis (RA) Patients from Fibromyalgia (FM) Patients and Both from Healthy Controls Based on Differential Effects of Pulsed Magnetic Fields (Cups; 200 µT) on Normal Standing.

Specific time varying pulsed magnetic fields (Cnps) have been shown to alter subjectively assessed animal and human behaviours, including pain perception. The differential response to specific pulsed magnetic fields was used on standing balance and other behavioural measures to separate normal control patients from patients with different diseases or pathologies.

Figure 2:
FIG. 2 shows a subject positioned within the magnetic field exposure system which includes three nested orthogonal Helmholtz coils (2 m, 1.75 m and 1.5 m diameter) wound on moveable Lexan® frames showing the coil array partially closed. The wheel track is shown in place (see A). During coil movement, the lower Z axis coil will be locked to the upper coil on the left side, permitting the subject to remain comfortably in a standing position throughout the protocol. For demonstration purposes only, the subject's right hand indicates the raised side of the lower Z axis coil.

Patients were recruited, 15 RA (mean ±SD 58±12.4; 5 male, 10 female) and 15 RA (mean ±SD 45±10.2; 15 female) from a university hospital outpatient rheumatology clinic. All patients met the most recent American College of Rheumatology (ACR) disease classification criteria Also recruited were 15 healthy controls (mean ±SD 31±7.4; 7 male, 8 female) from among university students and personnel. Each subject was placed within 3 square Helmholtz coils (2 m×1.75 m×1.5 m) (Thomas et al, 2000a), with each coil arranged orthogonal to the other two with the uniform magnetic field volume centred at head level for standing volunteers. FIG. 1, FIG. 2). Subjects blind to study intent and exposure conditions stood with feet approximately 10 cm apart on the centre of the 3D forceplate. All forceplate and Cnps (3D fluxgate magnetometer) values were continually digitally recorded at 20 samples per second. Each subject received four 2-minute exposure conditions (eyes open/closed, sham/Cnps) in a random order. Standing balance was measured during each of the four exposures. A "Romberg Quotient" (RQ) was calculated for sham and Cnps exposures as the cumulative area of movement during normal standing balance with the "eyes closed" condition divided by the "eyes open" condition. Data was analysed using ANOVA and post hoc testing.

Figure 3:
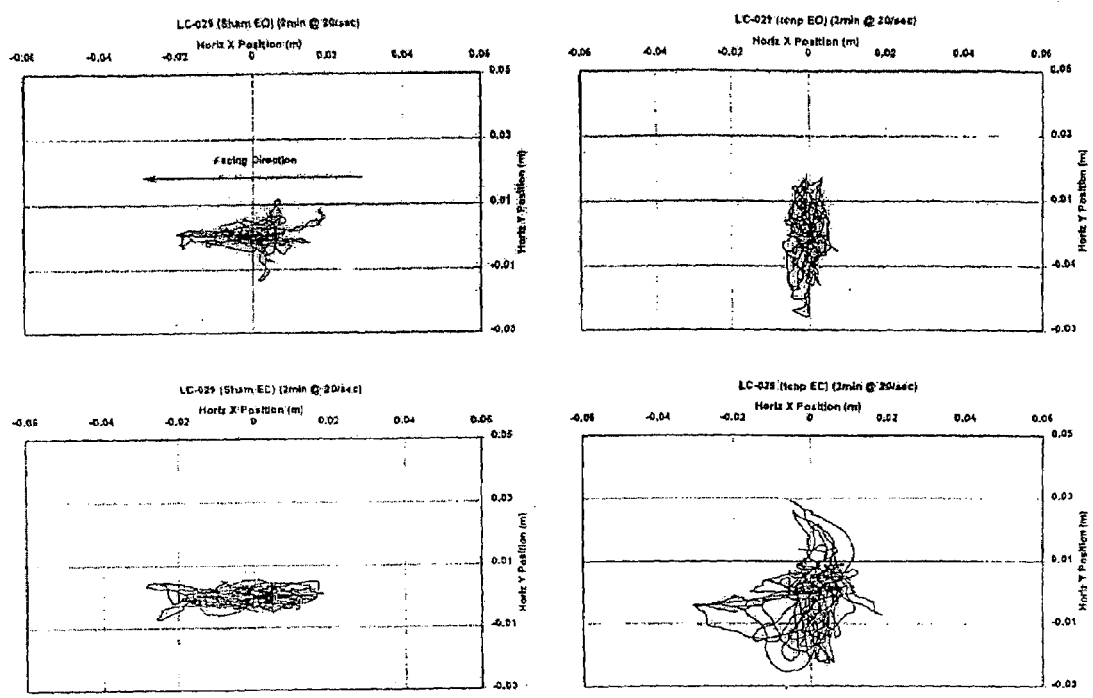
FIG. 3 shows raw forceplate data recorded real-time for blinded processing and analysis at a later time. The preliminary center of pressure (COP) is shown with data projected perpendicular through the forceplate with the line representing movement over time. Subjects, blind to the exposure condition, stand in the center of a forceplate mounted level to the surface of a sub-floor with feet slightly apart at a prescribed distance are randomly exposed to either a Sham or PEMF condition with either eyes-open or eyes-closed.

FIG. 3 shows a typical result in one patient with the pattern changing when the subject closes their eyes and when they are exposed to the Cnps. FIGS. 4, 5 and FIG. 6 provide the raw data, the RQ and results for 3 parameter reductions of the raw data. With eyes open and during sham exposure, FM patients and controls appeared to have similar standing balance while RA patients had worse standing balance (FIG. 4). With eyes closed, standing balance worsened for all three groups but more so for RA and FM patients than for controls (FIG. 4). The RQ was highest among FM patients (FIG. 5, FIG. 6). Mixed design analysis of variance on the centre of pressure (COP) measurements show a significant interaction of eyes open/closed and sham/Cnps conditions [F=8.78 (1,42), p<0.006]. RQ of COP measurements improved significantly with Cnps exposure [F=9.5 (1,42), p<0.005] and COP path length showed an interaction approaching significance with clinical diagnosis [F=3.2 (1,28), p<0.09].

From these sets of experiments it was evident that RA and FM patients and healthy controls differed with respect to standing balance and the effect of the Cnps. The separation of RA patients from FM patients is of significant value as these patients are often given the wrong classification, ie. FM patients diagnosed incorrectly as RA patients and vice versa, especially in the initial manifestation of the disease. The ability to separate both these patients from normal controls especially FM from normal controls is extremely important in the scenario of workmen's compensation benefits. Among the medical community and among health insurers there is concern that individuals without true pain, fatigue or disability can feign pain, fatigue and/or disability and hence, be inappropriately classified as FM patients and receive compensation. It is also possible that true FM patients may not receive compensation as they cannot be objectively categorized. As the method of the present invention is entirely objective, it provides for the first time a measure which can be used to determine compensation rights.

Example 2

Assessment of Pain and Analgesia in Subjects Exposed to a Magnetic Field

Ratios of electrical current (mA time point/mA baseline) were applied to the web of the left thumb required to produce a subjective "moderate" pain rating in male and female university students (N=11) while exposed to either a sham or pulsed magnetic field (FIG. 11). A ratio greater than 1 may be interpreted as an indication of analgesia (or hypoalgesia), and less than 1, hyperalgesia. Individual subjects were randomly assigned to either an analgesia-inducing magnetic field (MN) exposure (N=6) or postural sway altering MF group (N=6). Sham and MF exposure trials were held at least one week apart and both experimenter and subjects were kept blind to the exposure conditions until the completion of the study (double-blinded). Electric current recordings at each time point (15-60 min) were divided by the baseline reading taken at time point 0 (not shown). Time point 15 was a second control time point, with exposures (sham or MW) starting at time point 25. The results show a significant interaction between ME type (analgesia vs. postural sway) and exposure condition (sham vs. MF exposed) [$F_{1,9}$=8.9, P<0.032, Eta$_2$=0.64]. Error bars represent the S.E.M.

The above disclosure generally describes the present invention. A more complete understanding can be obtained by reference to the above specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

Bibliography

1. Barker A. T., Freeston I. L., Jalinous R., Jarratt J. A. *Magnetic stimulation of the human brain and peripheral nervous system: an introduction and the results of initial clinical evaluation*. Neurosurgery 1987, 20, 100-109.
2. Prato F. S., Kavaliers M. and Thomas A. W. *Extremely low frequency magnetic fields can either increase or decrease analgesia in the land snail depending on field and light conditions*. Bioelectromagnetics 2000; 21:1-15.
3. Choleris E., Thomas A. W. Davaliers M., Prato F. S. *A detailed ethological analysis of the mouse open field test: Effects of chlorodiazepoxide diazepam and extremely low frequency pulsed magnetic field*. Neuroscience and Behavioural Reviews 2001.

4. Thomas A. W., Drost D. J., Prato F. S. 2001a. *A magnetic field exposure and behavioural monitoring system*. Bioeletromagnetics in press.
5. Thomas A. W. Drost D. J., Prato F. S. 2001b. *Human subjects exposed to a specific pulsed magnetic field: effects on normal standing balance*. Neurosciences Letters. 297: 121-124.
6. Thomas A. W. White K. P. Drost D. J. Cook C. M., Prato F. S. 2001c. *A comparison of rheumatoid arthritis (RA) and fibromyalgia (FM) patients and healthy controls exposed to a pulsed magnetic field: effects on normal standing balance*. Neuroscience letters. Accepted.
7. Prato F. S., Thomas A. W., Cook C. M. 2001. *Human Standing balance is affected by exposure to pulsed ELF magnetic fields: light intensity dependent effects*. NevroReport (in press).

All publications, patents, and patent applications are incorporated by reference herein, as though individually incorporated by reference.

TABLE 1

Table of Romberg Quotients
(Mean ± 1 S.E.M.)

$$RQ_{Measure} = \frac{EyesClosed_{Measure}}{EyesOpen_{Measure}}$$

| Light Intensity: | 0.12 W/m² | | 0.51 W/m² | |
|---|---|---|---|---|
| Exposure: | Sham | PEMF | Sham | PEMF |
| Measure | | | | |
| Line: | 1.29 ± 0.14 | 1.78 ± 0.24* | 1.26 ± 0.08 | 1.14 ± 0.05* |
| Area: | 1.78 ± 0.37 | 3.79 ± 0.92* | 1.78 ± 0.21 | 1.44 ± 0.12* |
| Path: | 1.64 ± 0.14 | 1.88 ± 0.24 | 1.66 ± 0.10 | 1.69 ± 0.13 |

*Significantly different between Light Intensities
The interaction of Light Intensity and Exposure is significant (i.e. Line . . . $F_{1,33} = 11.8$, $P < 0.003$).

TABLE 3

Table of Results
(Mean ± 1 S.E.M.)

$$RQ_{Measure} = \frac{EyesClosed_{Measure}}{EyesOpen_{Measure}}$$

| Light Intensity: | 0.12 W/m² | | 0.51 W/m² | |
|---|---|---|---|---|
| Exposure: | Sham | PEMF | Sham | PEMF |
| Measure (Romberg Quotient, RQ) | | | | |
| Line: | 1.29 ± 0.14 | 1.78 ± 0.24* | 1.26 ± 0.08 | 1.14 ± 0.05* |
| Path: | 1.64 ± 0.14 | 1.88 ± 0.24 | 1.66 ± 0.10 | 1.69 ± 0.13 |

*Significantly different between Light Intensities
The interaction of Light Intensity and Exposure is SIGNIFICANT (LINE: $F_{1,33} = 11.8$, $p < 0.002$).

Direction Sensitivity (Mean Axis Shift Difference (m), PEMF-Sham)

| Light Intensity: | 0.12 W/m² | 0.51 W/m² |
|---|---|---|
| X axis : | EO 4.805E−04 ± 1.69E−03 | 9.517E−04 ± 6.45E−03 |
| | EC 2.154E−05 ± 3.06E−03 | 1.915E−03 ± 7.22E−04* |
| Y axis : | EO 5.670E−04 ± 1.25E−03 | 1.242E−03 ± 6.68E−04 |
| | EC 2.532E−04 ± 1.60E−03 | 1.903E−04 ± 8.40E−04 |

*Significantly different between Exposure condition only.
The interaction of Light Intensity and Exposure is not significant ($P > 0.65$).

TABLE 2

| | Pre-experiment, Mean (Std Dev) | | Post-experiment, Mean (Std Dev) | |
|---|---|---|---|---|
| | RA | FM | RA | FM |
| Binary Question (No = 0, Yes = 1) | | | | |
| Do you have pain in your shoulders, arms or hands? | 0.80 (0.41) | 0.86 (0.36) | 0.60 (0.51) | 0.86 (0.36) |
| Do you have pain in your hips, legs or feet? | 0.80 (0.41) | 1.00 (0.00) | 0.67 (0.49) | 0.86 (0.36) |
| Do you have pain in your neck? | 0.47 (0.52) | 0.86 (0.36)^ | 0.33 (0.49) | 0.79 (0.43)^ |
| Do you pain in your back? | 0.33 (0.49) | 0.93 (0.27)^ | 0.33 (0.49) | 0.86 (0.36)^ |
| Do you have pain elsewhere? | 0.40 (0.51) | 0.57 (0.51) | 0.40 (0.51) | 0.57 (0.51) |
| Analog Pain Scale (10 cm line) 0 = None, 10 = Very. | | | | |
| How bad is your pain RIGHT NOW? | 3.34 (2.09)↑ | 4.96 (1.94)^↑ | 2.87 (2.09) | 4.55 (2.50) |
| How bad is your stiffness RIGHT NOW? | 3.13 (2.77) | 4.36 (2.54) | 2.50 (1.44) | 4.28 (2.82)^ |
| How tired or fatigued are you RIGHT NOW? | 4.26 (2.91)↑ | 5.32 (2.75)↑ | 2.99 (2.03) | 4.56 (2.68) |
| How weak do you feel RIGHT NOW? | 2.67 (1.90) | 3.79 (2.40) | 2.78 (2.50) | 3.09 (2.67) |
| How tense, nervous or anxious do you feel RIGHT NOW? | 1.80 (2.06)↑ | 2.64 (2.16)↑ | 1.63 (1.63) | 1.77 (1.51) |
| How dizzy do you feel RIGHT NOW? | 2.14 (2.50) | 1.88 (1.93) | 1.94 (1.76) | 1.66 (1.62) |

^ relates to a significant difference (greater than, $P < 0.05$) between RA and FM within Pre- or Post-experiment testing.
↑ relates to a significant difference (greater than, $P < 0.05$) between Pre- and Post-experiment testing.

TABLE 4

FIG. 14—Summary of the effects of the first Magnetic field exposure on open field behavior

| | | OVERALL | | | TIME COURSE (ANOVA 0 × 1) | | | | | | | | | |
|---|---|---|---|---|---|---|---|---|---|---|---|---|---|---|
| | | | | | SHAM-1 | Mean Comparisons | | | | MAG-1 | Mean Comparisons | | | |
| | | ANOVA 1 × 1 | | | | 0-5 | 0-5 | 0-5 | 0-5 | | 0-5 | 0-5 | 0-5 | 0-5 |
| BEHAVIOR | | Time | Treatment | Tim × Tre | Time | vs 5-10 | vs 10-15 | vs 15-20 | vs 20-25 | vs 25-30 | Time | vs 5-10 | vs 10-15 | vs 15-20 | vs 20-25 | vs 25-30 |

Note: The actual column structure has Time appearing twice (once under SHAM-1, once under MAG-1).

| BEHAVIOR | | Time | Treat-ment | Tim × Tre | Time | 0-5 vs 5-10 | 0-5 vs 10-15 | 0-5 vs 15-20 | 0-5 vs 20-25 | 0-5 vs 25-30 | Time | 0-5 vs 5-10 | 0-5 vs 10-15 | 0-5 vs 15-20 | 0-5 vs 20-25 | 0-5 vs 25-30 |
|---|---|---|---|---|---|---|---|---|---|---|---|---|---|---|---|---|
| LOCATION | | | | | | | | | | | | | | | | |
| Corner + Wall | Du | H | ns | ns | H | ns | S | S | H | H | H | H | H | H | H | H |
| | Fre | H | H | ns | H | ns | ns | H | H | H | H | ns | S | S | H | S |
| Corner | Du | ns | ns | ns | ns | ns | ns | ns | ns | ns | ns | ns | ns | ns | ns | ns |
| | Fre | H | H | ns | H | ns | ns | S | H | H | H | ns | ns | S | H | H |
| Wall | Du | H | T | ns | S | ns | S | T | H | S | T | ns | S | S | H | S |
| | Fre | H | H | ns | H | ns | S | H | H | H | S | ns | T | ns | H | S |
| Outer ring | Du | H | ns | ns | S | ns | T | S | S | S | S | H | S | H | H | H |
| | Fre | ns | ns | ns | ns | ns | ns | ns | ns | ns | ns | ns | ns | ns | ns | ns |
| Inner ring | Du | H | ns | ns | S | ns | S | S | H | H | H | H | H | H | H | H |
| | Fre | H | ns | ns | S | ns | H | S | S | S | H | H | H | H | H | H |
| Central square | Du | H | ns | ns | H | H | H | S | H | H | H | S | H | H | H | H |
| | Fre | S | ns | ns | ns | ns | S | ns | S | T | ns | S | S | ns | ns | ns |
| Loco-motion Total | Du | H | H | ns | H | ns | ns | S | H | H | H | ns | H | S | H | H |
| | Fre | T | ns | ns | ns | ns | S | ns | ns | ns | H | ns | S | ns | ns | ns | ns |
| Explore Total | Du | H | ns | ns | S | ns | ns | S | S | S | H | ns | H | ns | S | H |
| | Fre | H | S | ns | ns | ns | ns | ns | ns | ns | H | ns | ns | ns | S | S |
| Corner | Du | H | S | ns | H | ns | T | H | H | H | H | H | H | H | H | H |
| | Fre | H | H | ns | H | S | H | H | H | H | H | H | H | H | H | H |
| Wall | Du | H | ns | ns | H | ns | ns | T | H | S | H | ns | H | S | H | H |
| | Fre | H | S | ns | H | ns | ns | ns | H | H | H | ns | H | S | H | H |
| Outer ring | Du | H | ns | ns | S | ns | S | S | S | S | T | S | T | H | S | S |
| | Fre | H | ns | ns | T | ns | S | T | S | T | H | H | H | H | T | S |
| Inner ring | Du | H | ns | ns | S | ns | S | S | H | H | H | H | H | H | H | H |
| | Fre | H | ns | ns | H | T | H | S | H | H | H | H | H | H | H | H |
| Central square | Du | H | ns | ns | H | H | H | S | H | H | S | T | H | S | H | H |
| | Fre | H | ns | ns | H | H | H | S | H | H | S | T | H | H | H | H |
| Walk Total | Du | ns | ns | ns | ns | ns | ns | ns | ns | ns | ns | ns | ns | ns | ns | ns |
| | Fre | ns | ns | ns | ns | ns | ns | ns | ns | ns | ns | ns | ns | ns | ns | ns |
| Corner | Du | ns | ns | ns | ns | ns | ns | ns | ns | ns | ns | T | ns | ns | T | ns |
| | Fre | ns | ns | ns | ns | ns | ns | ns | ns | ns | ns | ns | ns | ns | ns | ns |
| Wall | Du | ns | ns | ns | ns | ns | ns | ns | S | ns | ns | ns | ns | ns | ns | ns |
| | Fre | S | ns | ns | ns | ns | ns | ns | S | S | ns | ns | ns | ns | ns | S |
| Outer ring | Du | ns | ns | ns | ns | ns | ns | ns | ns | ns | ns | ns | T | T | H | S |
| | Fre | S | ns | ns | ns | ns | ns | ns | ns | ns | S | ns | T | S | H | S |
| Inner ring | Du | ns | ns | ns | ns | ns | ns | ns | ns | ns | T | ns | ns | S | S | S |
| | Fre | S | ns | ns | ns | ns | ns | ns | ns | ns | S | ns | ns | S | H | S |
| Central square | Du | S | ns | ns | ns | ns | ns | ns | T | ns | H | ns | ns | ns | H | S |
| | Fre | H | ns | ns | ns | ns | ns | ns | ns | ns | H | ns | ns | ns | H | H |
| Spin Turn Total | Du | H | ns | H | S | ns | ns | T | ns | ns | H | H | H | H | H | H |
| | Fre | H | ns | ns | T | ns | ns | T | ns | S | H | S | H | H | H | H |
| Corner | Du | ns | ns | ns | ns | ns | ns | ns | ns | ns | ns | ns | T | ns | ns | S |
| | Fre | ns | ns | ns | ns | ns | ns | ns | ns | ns | ns | ns | S | T | ns | S |
| Wall | Du | S | ns | ns | ns | ns | ns | S | ns | ns | S | ns | T | ns | H | H |
| | Fre | H | ns | ns | ns | ns | ns | S | ns | ns | H | ns | ns | ns | S | H |
| Groom Total | Du | H | H | ns | H | S | S | H | H | H | H | T | H | H | H | H |
| | Fre | H | ns | ns | H | S | ns | H | H | H | H | S | H | H | H | H |
| Corner | Du | H | ns | ns | S | H | S | H | S | H | S | T | H | S | ns | T |
| | Fre | H | ns | ns | H | S | S | S | S | H | S | S | S | S | S | H |
| Wall | Du | H | ns | ns | H | ns | ns | S | S | H | T | ns | ns | ns | S | ns |
| | Fre | H | ns | ns | H | ns | ns | S | S | H | T | ns | ns | ns | S | S |
| Sit Total | Du | S | ns | ns | S | ns | ns | ns | ns | H | ns | ns | ns | S | ns | ns |
| | Fre | T | ns | ns | ns | ns | ns | ns | ns | T | ns | ns | ns | S | ns | ns |
| Corner | Du | ns | ns | ns | S | ns | ns | ns | ns | H | ns | ns | ns | ns | ns | ns |
| | Fre | ns | ns | ns | ns | ns | ns | ns | ns | ns | ns | ns | ns | ns | ns | ns |
| Wall | Du | ns | ns | ns | ns | ns | ns | ns | ns | ns | ns | ns | ns | ns | ns | ns |
| | Fre | ns | S | ns | ns | ns | ns | T | ns | ns | ns | ns | ns | ns | ns | ns |
| Outer ring | Du | ns | ns | ns | ns | ns | ns | ns | ns | T | ns | ns | ns | ns | ns | ns |
| | Fre | ns | ns | ns | ns | / | / | / | ns | ns | ns | / | / | ns | ns | / |
| Stretch Attend Total | Fre | H | ns | ns | H | H | H | H | H | H | H | H | H | H | H | H |
| Corner | Fre | H | ns | ns | H | H | H | H | H | H | H | H | H | H | H | H |
| Wall | Fre | H | ns | ns | H | H | H | H | H | H | H | H | H | H | H | H |
| Outer ring | Fre | H | ns | ns | H | H | H | H | H | H | H | H | H | H | H | H |

TABLE 4-continued

FIG. 14—Summary of the effects of the first Magnetic field exposure on open field behavior

| | | | | | | | | | | | | | | | |
|---|---|---|---|---|---|---|---|---|---|---|---|---|---|---|---|
| Inner ring | Fre | H | ns | ns | T | S | ns | ns | T | S | H | ns | ns | H | H | H |
| Central squa | Fre | H | ns | ns | ns | T | ns | ns | ns | S | H | ns | ns | H | H | H |
| Return Total | Fre | H | ns | T | H | H | H | H | H | H | H | H | H | H | H | H |
| Corner | Fre | H | ns | ns | H | T | H | H | H | H | S | H | H | H | H | H |
| Wall | Fre | H | ns | T | H | H | H | H | H | H | H | H | H | H | H | H |
| Rear Total | Fre | H | ns | ns | H | S | H | H | H | H | H | H | H | H | H | H |
| Corner | Fre | S | ns | ns | ns | T | S | S | ns | ns | ns | S | ns | ns | ns | ns |
| Wall | Fre | H | ns | ns | H | S | H | H | H | H | H | H | H | H | H | H |
| Outer ring | Fre | H | ns | ns | H | ns | H | H | H | H | H | H | H | H | H | H |
| Inner ring | Fre | H | ns | ns | H | ns | H | H | H | H | H | H | H | H | H | H |
| Central squa | Fre | H | ns | ns | H | ns | S | ns | H | H | ns | ns | S | ns | S | S |

| | | DIRECT EFFECT OF TREATMENT MANOVA | | | | | |
|---|---|---|---|---|---|---|---|
| BEHAVIOR | | 0-5 | 5-10 | 10-15 | 15-20 | 20-25 | 25-30 |
| LOCATION | | | | | | | |
| Corner + Wall | Du | ns | ns | ns | ns | ns | ns |
| | Fre | H | H | H | S | T | S |
| Corner | Du | ns | ns | ns | ns | ns | ns |
| | Fre | T | ns | H | S | ns | T |
| Wall | Du | ns | ns | ns | ns | ns | ns |
| | Fre | H | H | S | S | ns | ns |
| Outer ring | Du | ns | ns | ns | ns | ns | ns |
| | Fre | T | ns | T | ns | ns | ns |
| Inner ring | Du | ns | ns | ns | ns | ns | ns |
| | Fre | S | ns | ns | ns | ns | ns |
| Central square | Du | ns | ns | ns | ns | ns | ns |
| | Fre | ns | ns | ns | ns | ns | ns |
| Loco-motion Total | Du | ns | T | H | ns | S | ns |
| | Fre | ns | ns | S | ns | ns | ns |
| Explore Total | Du | ns | ns | T | ns | ns | ns |
| | Fre | ns | ns | S | ns | ns | ns |
| Corner | Du | ns | S | S | S | ns | ns |
| | Fre | ns | S | H | S | ns | S |
| Wall | Du | ns | ns | ns | ns | ns | ns |
| | Fre | ns | ns | S | S | ns | ns |
| Outer ring | Du | ns | T | ns | ns | ns | ns |
| | Fre | ns | ns | ns | ns | ns | ns |
| Inner ring | Du | ns | ns | T | ns | ns | ns |
| | Fre | ns | ns | ns | ns | ns | ns |
| Central square | Du | ns | ns | ns | ns | ns | ns |
| | Fre | ns | ns | ns | ns | ns | ns |
| Walk Total | Du | ns | ns | ns | ns | ns | ns |
| | Fre | ns | ns | ns | ns | ns | ns |
| Corner | Du | ns | ns | ns | ns | ns | ns |
| | Fre | ns | ns | ns | ns | ns | ns |
| Wall | Du | ns | ns | ns | ns | ns | ns |
| | Fre | ns | ns | ns | ns | ns | ns |
| Outer ring | Du | ns | ns | ns | ns | ns | ns |
| | Fre | ns | ns | ns | ns | ns | ns |
| Inner ring | Du | ns | ns | ns | ns | ns | ns |
| | Fre | ns | ns | ns | ns | ns | ns |
| Central Square | Du | ns | ns | ns | ns | ns | ns |
| | Fre | ns | ns | ns | ns | ns | ns |
| Spin Turn Total | Du | ns | H | S | ns | ns | ns |
| | Fre | ns | ns | ns | ns | ns | ns |
| Corner | Du | ns | ns | ns | ns | ns | ns |
| | Fre | ns | ns | T | ns | ns | ns |
| Wall | Du | ns | ns | T | ns | ns | ns |
| | Fre | ns | ns | ns | T | ns | ns |
| Groom Total | Du | ns | ns | S | ns | S | ns |
| | Fre | ns | ns | T | ns | ns | ns |
| Corner | Du | ns | ns | ns | ns | ns | ns |
| | Fre | ns | ns | ns | ns | ns | ns |

TABLE 4-continued

FIG. 14—Summary of the effects of the first Magnetic field exposure on open field behavior

|  |  |  |  |  |  |  |  |
|---|---|---|---|---|---|---|---|
| Wall | Du | ns | ns | T | ns | ns | ns |
|  | Fre | ns | ns | ns | ns | ns | ns |
| Sit | Du | ns | ns | ns | ns | ns | ns |
| Total | Fre | ns | ns | ns | ns | ns | ns |
| Corner | Du | ns | ns | ns | ns | ns | ns |
|  | Fre | ns | ns | ns | T | ns | ns |
| Wall | Du | ns | ns | ns | ns | ns | ns |
|  | Fre | ns | ns | ns | ns | ns | ns |
| Outer ring | Du | / | / | / | ns | ns | ns |
|  | Fre | / | / | / | ns | ns | ns |
| Stretch Attend Total | Fre | ns | ns | ns | ns | ns | ns |
| Corner | Fre | ns | ns | ns | ns | ns | ns |
| Wall | Fre | ns | T | ns | ns | ns | ns |
| Outer ring | Fre | ns | ns | ns | ns | ns | ns |
| Inner ring | Fre | ns | ns | ns | ns | T | ns |
| Central squa | Fre | ns | S | ns | ns | ns | ns |
| Return Total | Fre | T | ns | ns | ns | ns | ns |
| Corner | Fre | ns | T | ns | / | / | / |
| Wall | Fre | T | ns | ns | ns | ns | ns |
| Rear Total | Fre | ns | ns | ns | ns | ns | ns |
| Corner | Fre | ns | ns | ns | T | ns | ns |
| Wall | Fre | ns | ns | ns | ns | ns | ns |
| Outer ring | Fre | ns | ns | ns | ns | ns | ns |
| Inner ring | Fre | ns | ns | ns | ns | ns | ns |
| Central squa | Fre | ns | ns | ns | ns | ns | ns |

TABLE 5

FIG. 15—Summary of the effects of the second Magnetic field exposure on open field behavior

| | | OVERALL | | | TIME COURSE (ANOVA 0 × 1) | | | | | | | | | |
|---|---|---|---|---|---|---|---|---|---|---|---|---|---|---|
| | | | | | SHAM-2 | | Mean Comparisons | | | | MAG-2 | | Mean Comparisons | |
| | | ANOVA 1 × 1 | | | 0-5 | 0-5 | 0-5 | 0-5 | 0-5 | 0-5 | | 0-5 | 0-5 | 0-5 | 0-5 | 0-5 |
| BEHAVIOR | | Time | Treatment | Tim × Tre | Time | vs 5-10 | vs 10-15 | vs 15-20 | vs 20-25 | vs 25-30 | Time | vs 5-10 | vs 10-15 | vs 15-20 | vs 20-25 | vs 25-30 |
| LOCATION | | | | | | | | | | | | | | | | |
| Corner + Wall | Du | H | ns | ns | H | T | H | H | H | T | H | H | H | H | H |
|  | Fre | S | ns | ns | ns | ns | T | S | ns | ns | T | ns | ns | ns | ns |
| Corner | Du | ns | ns | ns | ns | ns | ns | ns | ns | ns | ns | ns | ns | ns | S | ns |
|  | Fre | ns | ns | ns | ns | ns | ns | ns | ns | ns | ns | ns | ns | ns | ns |
| Wall | Du | H | ns | ns | S | ns | ns | ns | H | S | S | ns | S | ns | ns | H |
|  | Fre | ns | ns | ns | ns | ns | ns | ns | ns | ns | T | ns | ns | ns | ns | T |
| Outer ring | Du | H | ns | ns | H | H | H | H | H | H | H | H | H | H | H |
|  | Fre | ns | ns | ns | ns | ns | ns | ns | ns | ns | ns | ns | ns | ns | S |
| Inner ring | Du | H | ns | ns | T | ns | S | H | S | ns | H | H | H | H | H |
|  | Fre | H | ns | ns | H | H | H | H | H | H | H | H | H | H | H |
| Central square | Du | H | ns | ns | S | H | S | H | ns | ns | H | H | H | H | S |
|  | Fre | S | ns | ns | ns | ns | ns | ns | ns | ns | H | S | ns | ns | ns |
| Locomotion Total | Du | H | T | ns | H | ns | ns | T | H | H | H | S | H | H | H | H |
|  | Fre | H | T | T | S | H | H | ns | S | H | H | H | H | H | H | S |
| Explore Total | Du | H | ns | ns | H | ns | S | H | H | H | H | ns | S | T | H |
|  | Fre | H | ns | T | H | ns | ns | ns | T | T | H | S | ns | S | ns |
| Corner | Du | H | T | ns | H | S | H | H | H | H | H | S | H | H | H | H |
|  | Fre | H | ns | ns | H | ns | S | H | H | H | H | ns | S | H | H | H |
| Wall | Du | H | ns | ns | H | ns | S | H | H | H | H | ns | S | H | H | H |
|  | Fre | H | ns | S | H | ns | ns | ns | H | H | H | S | ns | ns | ns | H |
| Outer ring | Du | H | ns | ns | H | S | H | H | H | S | H | H | H | H | H |
|  | Fre | H | ns | ns | H | H | H | H | S | T | H | H | H | H | H |
| Inner ring | Du | H | ns | ns | ns | ns | S | S | ns | ns | H | H | H | H | S |
|  | Fre | H | ns | ns | H | H | H | H | S | T | H | H | H | H | H |

TABLE 5-continued

FIG. 15—Summary of the effects of the second Magnetic field exposure on open field behavior

| | | | | | | | | | | | | | | | |
|---|---|---|---|---|---|---|---|---|---|---|---|---|---|---|---|
| Central | Du | H | ns | ns | S | H | S | S | ns | ns | H | H | H | H | H | S |
| square | Fre | H | ns | ns | T | S | S | S | T | ns | H | S | H | H | H | S |
| Walk | Du | ns | ns | ns | ns | ns | ns | ns | ns | ns | ns | T | ns | ns | S | ns |
| Total | Fre | H | ns | ns | ns | ns | S | T | T | S | S | S | S | ns | H | T |
| Corner | Du | H | ns | ns | S | ns | ns | H | S | S | S | ns | S | H | S | H |
| | Fre | H | ns | ns | S | ns | ns | T | ns | ns | S | ns | ns | T | ns | ns |
| Wall | Du | ns | ns | ns | ns | ns | ns | ns | ns | ns | ns | T | ns | ns | ns | ns |
| | Fre | ns | ns | ns | ns | ns | ns | ns | ns | ns | S | ns | ns | ns | ns | ns |
| Outer | Du | H | ns | ns | H | ns | H | H | H | H | H | ns | S | S | H | H |
| ring | Fre | H | ns | ns | H | T | H | H | H | H | H | ns | H | H | H | H |
| Inner | Du | H | ns | ns | H | ns | S | S | H | H | H | ns | ns | S | H | S |
| ring | Fre | H | ns | ns | H | ns | S | S | H | H | H | ns | S | H | H | H |
| Central | Du | S | ns | ns | T | ns | ns | H | S | S | ns | ns | ns | ns | ns | S |
| square | Fre | H | ns | ns | S | ns | ns | H | S | S | ns | ns | ns | ns | ns | S |
| Spin Turn | Du | H | ns | H | H | ns | H | S | H | H | H | H | ns | S | ns | S |
| Total | Fre | | | | | | | | | | | | | | | |
| Corner | Du | ns | H | ns | ns | ns | S | ns | S | S | ns | ns | ns | T | ns | ns |
| | Fre | S | S | ns | ns | ns | S | ns | S | S | T | ns | T | H | ns | ns |
| Wall | Du | H | ns | ns | ns | ns | S | ns | ns | S | S | ns | S | H | ns | T |
| | Fre | H | ns | ns | S | ns | H | ns | S | H | H | ns | H | H | H | S |
| Groom | Du | H | H | ns | H | S | H | H | H | H | H | S | H | H | H | H |
| Total | Fre | H | S | ns | H | S | H | H | H | H | H | H | H | H | H | H |
| Corner | Du | H | ns | ns | ns | ns | S | S | S | S | H | ns | H | H | ns | H |
| | Fre | H | ns | ns | ns | ns | S | S | S | S | H | S | H | H | S | H |
| Wall | Du | H | S | ns | S | ns | ns | T | S | H | ns | ns | ns | S | ns | S |
| | Fre | H | S | ns | H | ns | S | S | S | H | ns | ns | ns | S | T | ns |
| Sit | Du | ns | ns | ns | ns | ns | ns | ns | ns | ns | ns | ns | ns | ns | T | T |
| Total | Fre | S | ns | ns | ns | ns | ns | S | ns | ns | T | ns | ns | S | S | S |
| Corner | Du | ns | ns | ns | ns | ns | ns | ns | ns | ns | ns | ns | ns | ns | ns | ns |
| | Fre | ns | ns | ns | ns | ns | ns | ns | T | ns | ns | ns | ns | ns | ns | ns |
| Wall | Du | S | S | ns | ns | ns | ns | ns | ns | ns | ns | ns | T | ns | ns | ns |
| | Fre | ns | ns | ns | ns | ns | ns | ns | ns | ns | ns | ns | ns | S | ns | T |
| Outer | Du | ns | ns | ns | ns | ns | ns | T | ns | ns | ns | ns | ns | ns | ns | ns |
| ring | Fre | ns | ns | ns | ns | ns | ns | S | ns | ns | ns | ns | ns | ns | ns | ns |
| Stretch | Fre | H | ns | ns | H | H | H | H | H | H | H | H | H | H | H | H |
| Attend | | | | | | | | | | | | | | | | |
| Total | | | | | | | | | | | | | | | | |
| Corner | Fre | H | ns | ns | H | H | H | H | H | H | H | H | H | H | H | H |
| Wall | Fre | H | ns | ns | H | H | H | H | H | H | H | H | H | H | H | H |
| Outer | Fre | H | ns | ns | H | H | H | H | H | H | H | H | H | H | H | H |
| ring | | | | | | | | | | | | | | | | |
| Inner | Fre | H | ns | ns | T | S | ns | T | T | H | H | ns | ns | H | H | H |
| ring | | | | | | | | | | | | | | | | |
| Central | Fre | H | ns | ns | ns | T | ns | ns | ns | S | H | ns | ns | H | H | H |
| squa | | | | | | | | | | | | | | | | |
| Return | Fre | H | ns | T | H | H | H | H | H | H | H | H | H | H | H | H |
| Total | | | | | | | | | | | | | | | | |
| Corner | Fre | H | ns | T | H | H | H | H | H | H | S | ns | H | H | H | H |
| Wall | Fre | H | ns | ns | H | H | H | H | H | H | H | H | H | H | H | H |
| Rear | Fre | H | ns | ns | H | H | H | H | H | H | H | H | H | H | H | H |
| Total | | | | | | | | | | | | | | | | |
| Corner | Fre | H | ns | ns | H | H | H | H | H | H | H | H | H | H | H | H |
| Wall | Fre | H | ns | ns | H | H | H | H | H | H | H | H | H | H | H | H |
| Outer | Fre | H | ns | ns | H | H | H | H | H | H | H | H | H | H | H | H |
| ring | | | | | | | | | | | | | | | | |
| Inner | Fre | H | ns | ns | H | H | H | H | H | H | H | T | H | H | H | H |
| ring | | | | | | | | | | | | | | | | |
| Central | Fre | H | T | ns | S | ns | H | S | S | S | H | ns | ns | H | H | T |
| squa | | | | | | | | | | | | | | | | |

| | | DIRECT EFFECT OF TREATMENT MANOVA | | | | | |
|---|---|---|---|---|---|---|---|
| BEHAVIOR | | 0-5 | 5-10 | 10-15 | 15-20 | 20-25 | 25-30 |
| LOCATION | | | | | | | |
| Corner + | Du | ns | ns | ns | ns | ns | ns |
| Wall | Fre | ns | ns | ns | ns | ns | ns |
| Corner | Du | ns | ns | ns | ns | ns | ns |
| | Fre | ns | ns | ns | ns | ns | ns |
| Wall | Du | ns | ns | ns | ns | ns | ns |
| | Fre | T | ns | ns | ns | ns | ns |
| Outer | Du | ns | ns | ns | ns | ns | ns |
| ring | Fre | ns | ns | ns | ns | ns | ns |

TABLE 5-continued

FIG. 15—Summary of the effects of the second Magnetic field exposure on open field behavior

| | | | | | | | |
|---|---|---|---|---|---|---|---|
| Inner ring | Du | ns | ns | ns | ns | ns | ns |
| | Fre | ns | ns | ns | ns | ns | ns |
| Central square | Du | ns | ns | ns | ns | T | ns |
| | Fre | ns | T | ns | ns | ns | ns |
| Loco-motion Total | Du | T | T | S | ns | ns | ns |
| | Fre | T | S | ns | ns | ns | ns |
| Explore Total | Du | ns | ns | ns | ns | ns | ns |
| | Fre | ns | ns | ns | ns | ns | ns |
| Corner | Du | ns | ns | T | ns | ns | T |
| | Fre | ns | ns | ns | ns | ns | ns |
| Wall | Du | ns | ns | ns | ns | ns | ns |
| | Fre | ns | ns | ns | ns | ns | ns |
| Outer ring | Du | ns | ns | ns | ns | ns | ns |
| | Fre | ns | ns | ns | ns | ns | ns |
| Inner ring | Du | ns | ns | ns | ns | ns | ns |
| | Fre | ns | ns | ns | ns | ns | ns |
| Central square | Du | ns | ns | ns | ns | T | ns |
| | Fre | ns | ns | ns | ns | ns | ns |
| Walk Total | Du | ns | ns | ns | ns | ns | ns |
| | Fre | ns | ns | ns | ns | ns | ns |
| Corner | Du | ns | ns | ns | ns | ns | ns |
| | Fre | ns | ns | ns | ns | ns | ns |
| Wall | Du | ns | ns | ns | ns | ns | ns |
| | Fre | ns | ns | ns | ns | ns | ns |
| Outer ring | Du | ns | ns | ns | ns | ns | ns |
| | Fre | ns | ns | ns | T | ns | ns |
| Inner ring | Du | / | ns | ns | ns | ns | ns |
| | Fre | / | ns | ns | ns | ns | ns |
| Central square | Du | / | ns | ns | ns | ns | ns |
| | Fre | / | ns | ns | ns | ns | ns |
| Spin Turn Total | Du | T | S | ns | S | ns | ns |
| | Fre | T | ns | ns | T | ns | ns |
| Corner | Du | H | ns | ns | H | ns | ns |
| | Fre | S | ns | ns | H | ns | ns |
| Wall | Du | ns | ns | S | ns | ns | ns |
| | Fre | ns | ns | ns | T | ns | ns |
| Groom Total | Du | ns | ns | S | ns | S | ns |
| | Fre | S | S | ns | ns | ns | ns |
| Corner | Du | ns | ns | T | ns | ns | ns |
| | Fre | ns | ns | T | ns | ns | ns |
| Wall | Du | S | ns | ns | ns | ns | ns |
| | Fre | S | ns | ns | T | ns | ns |
| Sit Total | Du | ns | ns | ns | ns | T | ns |
| | Fre | ns | ns | ns | ns | ns | ns |
| Corner | Du | ns | ns | ns | ns | ns | ns |
| | Fre | ns | ns | ns | ns | ns | ns |
| Wall | Du | ns | ns | ns | ns | ns | ns |
| | Fre | ns | ns | ns | ns | ns | ns |
| Outer ring | Du | ns | ns | ns | ns | ns | ns |
| | Fre | ns | ns | ns | ns | ns | ns |
| Stretch Attend Total | Fre | ns | ns | ns | ns | ns | ns |
| Corner | Fre | ns | ns | ns | ns | ns | ns |
| Wall | Fre | ns | ns | ns | ns | ns | ns |
| Outer ring | Fre | ns | ns | ns | ns | ns | ns |
| Inner ring | Fre | ns | ns | ns | T | ns | |
| Central squa | Fre | ns | S | ns | ns | ns | ns |
| Return Total | Fre | T | ns | ns | / | / | / |
| Corner | Fre | ns | ns | / | / | / | / |
| Wall | Fre | ns | ns | ns | ns | / | / |
| Rear Total | Fre | ns | ns | T | T | ns | ns |
| Corner | Fre | ns | ns | T | ns | ns | ns |
| Wall | Fre | ns | ns | ns | ns | ns | ns |
| Outer ring | Fre | S | S | ns | ns | ns | ns |
| Inner ring | Fre | ns | ns | ns | ns | ns | ns |
| Central squa | Fre | / | ns | H | ns | ns | ns |

The invention claimed is:

1. A method for diagnosing a disease condition in a subject comprising:
   exposing the subject to a complex neuro-electro magnetic pulse (Cnps) for a period of time effective to produce a change in a physiological function;
   evaluating or assessing the change; and
   diagnosing a presence of the disease condition based on the evaluation or assessment of the change;
wherein the pulse is non-therapeutic for the disease condition.

2. The method of claim 1, wherein said complex neuro-electro magnetic pulse (Cnps) is targeted to a specific body part or tissue.

3. The method of claim 2, wherein said complex neuro-electro magnetic pulse (Cnps) is selected to affect a specific physiological function.

4. The method of claim 3, wherein said physiological function is a motor function or a cognitive function.

5. The method of claim 4, wherein said disease condition is a peripheral disorder.

6. The method of claim 5, wherein said peripheral disorder is rheumatoid arthritis, fibromyalgia, muscular dystrophy or general pain.

7. The method of claim 3, wherein the physiological function is balance.

8. The method of claim 7, wherein the disease condition is diagnosed to be either rheumatoid arthritis or fibromyalgia.

9. The method of claim 1, wherein said method is used to diagnose disability.

10. The method of claim 1, wherein a change in the physiological function is assessed objectively or subjectively.

11. A method for diagnosing or assessing a disease condition in a subject comprising:
    exposing said subject simultaneously to a complex neuro-electro magnetic pulse (Cnps) and a first prescribed light intensity and frequency distribution while monitoring a physiological function;
    exposing said subject a second time simultaneously to said complex neuro-electro magnetic pulse (Cnps) and a different light intensity of the same or different frequency distribution as said first prescribed light intensity while monitoring the physiological function;
    evaluating or assessing a change in the physiological function; and
    diagnosing a presence of the disease condition based on the evaluation or assessment of the change in the physiological function;
wherein the pulse is non-therapeutic for the disease condition.

12. A method for the diagnosing or assessing of a disease condition in a subject comprising:
    exposing said subject to a first complex neuro-electro magnetic pulse (Cnps) while monitoring a physiological function;
    exposing said subject a second time to a second selected complex neuro-electro magnetic pulse (Cnps) while monitoring the physiological function;
    evaluating or assessing a change in the physiological function; and
    diagnosing presence of the disease condition based on the evaluation or assessment of the change;
wherein at least one of the first pulse and the second pulse is non-therapeutic for the disease condition.

13. A method for diagnosing a disease condition in a subject comprising:
    evaluating a physiological function that is not a symptom of the disease condition in a subject;
    exposing said subject to a selected complex neuro-electro magnetic pulse (Cnps);
    evaluating or assessing a change in the physiological function; and
    diagnosing the presence of the disease condition based on the evaluation or assessment of the change in the physiological function;
wherein the pulse is non-therapeutic for the disease condition.

14. A method for diagnosing a disease condition in a subject comprising:
    exposing said subject simultaneously to two or more selected complex neuro-electro magnetic pulses (Cnps) while monitoring at least one physiological function;
    evaluating or assessing a change in the at least one physiological function; and
    diagnosing presence of the disease condition based on the evaluation or assessment of the change in the physiological function;
wherein the pulses are non-therapeutic for the disease condition.

15. The method of any one of claims 11, 12, 13 or 14, wherein said complex neuro-electro magnetic pulse (Cnps) is targeted to a specific body part or tissue.

16. The method of any one of claims 11, 12, 13 or 14, wherein said complex neuro-electro magnetic pulse (Cnps) is selected to affect a specific physiological function.

17. The method of claim 16, wherein said physiological function is a motor function or a cognitive function.

18. The method of claim 17, wherein said disease condition is a peripheral disorder.

19. The method of claim 18, wherein said peripheral disorder is rheumatoid arthritis, fibromyalgia, muscular dystrophy or general pain.

20. The method of any one of claims 11, 12, 13 or 14, wherein said method is used to diagnose a disability.

21. The method of any one of claims 11, 12, 13 or 14, wherein a change in the physiological function is assessed objectively or subjectively.

* * * * *